(12) United States Patent
Yan et al.

(10) Patent No.: US 9,561,387 B2
(45) Date of Patent: Feb. 7, 2017

(54) AMBIGUITY-FREE OPTICAL TRACKING SYSTEM

(71) Applicant: University of Florida Research Foundation, Inc., Gainesville, FL (US)

(72) Inventors: Guanghua Yan, Gainesville, FL (US); Bo Lu, Gainesville, FL (US); Chihray Liu, Gainesville, FL (US); Jonathan G. Li, Gainesville, FL (US)

(73) Assignee: Unitversity of Florida Research Foundation, Inc., Gainesville, FL (US)

( * ) Notice: Subject to any disclaimer, the term of this patent is extended or adjusted under 35 U.S.C. 154(b) by 249 days.

(21) Appl. No.: 14/394,353

(22) PCT Filed: Apr. 12, 2013

(86) PCT No.: PCT/US2013/036331
§ 371 (c)(1),
(2) Date: Oct. 14, 2014

(87) PCT Pub. No.: WO2013/155388
PCT Pub. Date: Oct. 17, 2013

(65) Prior Publication Data
US 2015/0085072 A1   Mar. 26, 2015

Related U.S. Application Data

(60) Provisional application No. 61/623,395, filed on Apr. 12, 2012.

(51) Int. Cl.
H04N 15/00 (2006.01)
H04N 13/00 (2006.01)
(Continued)

(52) U.S. Cl.
CPC ............... *A61N 5/1048* (2013.01); *A61B 6/03* (2013.01); *A61B 6/583* (2013.01); *A61N 5/107* (2013.01);
(Continued)

(58) Field of Classification Search
None
See application file for complete search history.

(56) References Cited

U.S. PATENT DOCUMENTS 5,825,947 A * 10/1998 Sasaki ..................... G06T 5/006
235/456
6,279,579 B1   8/2001 Riaziat et al.
(Continued)

FOREIGN PATENT DOCUMENTS

EP   2377576    10/2011
WO   99/30182    6/1999

OTHER PUBLICATIONS

International Search Report and Written Opinion dated Aug. 29, 2013, received for PCT Application No. PCT/US2013/036331.
(Continued)

*Primary Examiner* — Frederick Bailey
*Assistant Examiner* — Talha M Nawaz
(74) *Attorney, Agent, or Firm* — Fleit Gibbons Gutman Bongini Bianco PL; Jon A. Gibbons

(57) ABSTRACT

An ambiguity-free optical tracking system (100) includes a position sensor unit (104), a control box (106), a computer (110) and software. The position sensor unit includes two cameras (121 and 122) that track a plurality of individual infra-red reflecting markers (160) affixed on a patient's skin. Coordinates of the cameras in a coordinate system of the cameras are determined as part of a system calibration process by intentionally creating ambiguous markers with two true markers. Using this information, an ambiguity
(Continued)

elimination algorithm automatically identifies and eliminates ambiguous markers. A recursive backtracking algorithm builds a one-to-one correspondence between reference markers and markers optically observed during treatment. By utilizing a concept of null markers, the backtracking algorithm deals with missing, misplaced and occluded markers.

6 Claims, 10 Drawing Sheets

(51) Int. Cl.
| | |
|---|---|
| A61N 5/10 | (2006.01) |
| A61B 6/03 | (2006.01) |
| G01S 17/48 | (2006.01) |
| G01S 17/66 | (2006.01) |
| G01S 17/87 | (2006.01) |
| A61B 6/00 | (2006.01) |
| G01B 11/25 | (2006.01) |

(52) U.S. Cl.
CPC ........... *A61N 5/1049* (2013.01); *G01B 11/254* (2013.01); *G01S 17/48* (2013.01); *G01S 17/66* (2013.01); *G01S 17/87* (2013.01); *H04N 13/0048* (2013.01); *A61N 2005/1051* (2013.01); *A61N 2005/1059* (2013.01); *A61N 2005/1074* (2013.01)

(56) References Cited

U.S. PATENT DOCUMENTS

| | | | |
|---|---|---|---|
| 6,490,473 B1 | 12/2002 | Katznelson et al. | |
| 6,535,574 B1 | 3/2003 | Collins et al. | |
| 6,775,404 B1 | 8/2004 | Pagoulatos et al. | |
| 7,024,237 B1 | 4/2006 | Bova et al. | |
| 7,204,254 B2 | 4/2007 | Riaziat et al. | |
| 7,535,411 B2 | 5/2009 | Falco | |
| 7,657,303 B2 | 2/2010 | Mate et al. | |
| 7,715,606 B2 | 5/2010 | Jeung et al. | |
| 7,729,472 B2 | 6/2010 | Scherch et al. | |
| 7,881,767 B2 | 2/2011 | Strommer et al. | |
| 2002/0044204 A1* | 4/2002 | Zurl | G01S 5/163 348/169 |
| 2004/0138556 A1 | 7/2004 | Cosman | |
| 2004/0158146 A1 | 8/2004 | Mate et al. | |
| 2006/0215813 A1 | 9/2006 | Scherch et al. | |
| 2007/0287911 A1 | 12/2007 | Haid et al. | |
| 2008/0033283 A1 | 2/2008 | Dellaca et al. | |
| 2008/0095416 A1 | 4/2008 | Jeung et al. | |
| 2008/0132785 A1 | 6/2008 | Piron et al. | |
| 2008/0287728 A1 | 11/2008 | Mostafavi et al. | |
| 2008/0287783 A1 | 11/2008 | Anderson | |
| 2008/0317313 A1* | 12/2008 | Goddard | A61B 5/721 382/131 |
| 2009/0039886 A1 | 2/2009 | White | |
| 2009/0088622 A1 | 4/2009 | Mostafavi | |
| 2010/0008467 A1 | 1/2010 | Dussault et al. | |
| 2010/0010703 A1* | 1/2010 | Coats | G05D 1/024 701/29.6 |
| 2011/0230755 A1 | 9/2011 | MacFarlane et al. | |
| 2011/0306863 A1 | 12/2011 | Koshnitsky et al. | |

OTHER PUBLICATIONS

International Preliminary Report on Patentability dated Oct. 14, 2014 received for PCT Application No. PCT/US2013/036331.
Meeks, S., et al., "Optically Guided Patient Positioning Techniques", Seminars in Radiation Oncology, Jul. 2005, pp. 192-201, vol. 15, Issue 3. doi:10.1016/j.semradonc.2005.01.004.
Wagner, T., et al., "Optical Tracking Technology in Stereotactic Radiation Therapy", Medical Dosimetry, Jan. 2007, pp. 111-120, vol. 32, No. 2. doi:10.1016/j.meddos.2007.01.008.
Soete, G., et al., "Initial Clinical Experience With Infrared-Reflecting Skin Markers in the Positioning of Patients Treated by Conformal Radiotherapy for Prostate Cancer", Int. J. Radiation Oncology Biol. Phys., Sep. 2001, pp. 694-698, vol. 52, No. 3.
Benedict, S., et al., "Stereotactic body radiation therapy: The report of AAPM Task Group 101," Medical Physics, Aug. 2010, pp. 4078-4101, vol. 37, Issue 8.
Keall, P., et al., "The management of respiratory motion in radiation oncology report of AAPM Task Group 76," Medical Physics, Jul. 2006, pp. 3874-3900, vol. 33.
Walter, C., et al., "Phantom and in-vivo measurements of dose exposure by image-guided radiotherapy (IGRT): MV portal images vs. kV portal images vs. cone-beam CT," Radiotherapy and Oncology, Nov. 2007, pp. 418-423, vol. 85.
Yin, F., et al., "Integration of Cone-Beam CT in Stereotactic Body Radiation Therapy," Technology in Cancer Research and Treatment, Apr. 2008, pp. 133-139, vol. 7, No. 2.
Kim, H., et al., "Development of an optical-based image guidance system: Technique detecting external markers behind a full facemask," Medical Physics, May 27, 2011, pp. 3006-3012, vol. 38, No. 06.
Bova, F., et al., "The University of Florida Frameless High-Precision Stereotactic Radiotherapy System," International Journal of Radiation Oncology Biology Physics, Feb. 26, 1997, pp. 875-882, vol. 38, No. 04.
Ryken, T., et al., "Initial Clinical Experience With Frameless Stereotactic Radiosurgery: Analysis of Accuracy and Feasibility," International Journal of Radiation Oncology Biology Physics, Jul. 2001, pp. 1152-1158. vol. 51, Issue 4.
Tome, W., et al., "A High-Precision System for Conformal Intracranial Radiotherapy," International Journal of Radiation Oncology Biology Physics, Dec. 7, 1999, pp. 1137-1143, vol. 47, No. 4.
Baroni, G., et al., "Implementation and application of real-time motion analysis based on passive markers," Medical & Biological Engineering & Computing, Nov. 1998, pp. 693-703, vol. 36.
Baroni, G., et al., "Real-time three-dimensional motion analysis for patient positioning verification," Radiotherapy & Oncology, Nov. 12, 1999, pp. 21-27, vol. 54.
Yan, H., "The correlation evaluation of a tumor tracking system using multiple external markers," Medical Physics, Oct. 16, 2006, pp. 4073-4084, vol. 33, No. 11.
Stroian, G., et al., "Elimination of ghost markers during dual sensor-based infrared tracking of multiple individual reflective markers," Medical Physics, Jun. 22, 2004, pp. 2008-2019, vol. 31, Issue 07.
Yan, G., et al., "Ghost marker detection and elimination in marker-based optical tracking systems for real-time tracking in stereotactic body radiotherapy," Medical Physics, Oct. 1, 2014, pp. 1-11, vol. 41, No. 10.
International Preliminary Report on Patentability dated Oct. 14, 2014, received for PCT Application No. PCT/US2013/036340.
International Search Report & Written Opinion dated Aug. 1, 2013, received for PCT Application No. PCT/US2013/036340.
Qian, J., et al., "Dose Verification for respiratory-gated Volumetric modulated arc therapy (VMAT)," Aug. 7, 2011, pp. 4827-4838.

* cited by examiner

Reference marker set *A*        Optical marker set *B*

AMBIGUITY-FREE OPTICAL TRACKING SYSTEM

CROSS-REFERENCE TO RELATED APPLICATIONS

This application is based upon and claims priority to U.S. Provisional Patent Application Serial No. 61/623,395, entitled "DEVELOPMENT AND EVALUATION OF AN AMBIGUITY-FREE TRACKING SYSTEM FOR EXPANDED USE IN RADIOTHERAPY", filed Apr. 12, 2012, the disclosure of which is hereby incorporated by reference in its entirety.

STATEMENT REGARDING FEDERALLY SPONSORED RESEARCH

None.

FIELD OF THE INVENTION

The present invention generally relates to the field of radiotherapy, and more particularly to optical tracking systems.

BACKGROUND OF THE INVENTION

In targeted radiation therapy such as intensity-modulated radiation therapy (IMRT) and stereotactic body radiation therapy (SBRT), it is critical to position a patient in a treatment position accurately and reproducibly. It is also highly desirable to have accurate and continuous localization of the patient throughout radiation delivery, especially for a patient having lesions in thoracic and abdominopelvic region. It is not uncommon to observe abrupt patient motion due to patient voluntary movement, cough, irregular breathing, or dyspnea. Without accurate and continuous monitoring of the patient, it is difficult to decide if the patient displacement is within the tolerance margin.

Known x-ray based image guidance systems provide adequate accuracy for initial patient positioning, but most of them are not appropriate for real-time and continuous monitoring during the treatment. Fluoroscopy makes it possible to view internal organ motion in real time with the help of surgical clips or fiducial markers. But continuous fluoroscopy during long treatment durations is associated with the risk of excessive radiation exposure to the patient. Gantry-mounted, kilovoltage cone-beam computed tomography (CBCT) systems are quickly gaining popularity for patient positioning and target localization due to its superb capability of visualizing a soft-tissue target. However, CBCT is limited to an angle of a treatment couch of 0° and CBCT cannot acquire images in real-time.

Optical tracking systems present an attractive solution for continuous monitoring of patient during radiation delivery. There are two types of optical tracking systems developed for the purpose of radiotherapy: 1) a body marker-based optical tracking system uses infrared (IR) light to detect target position via active or passive reflective markers affixed to the patient, and 2) a three-dimensional (3D), surface image-based optical tracking system that captures patient surface images in real time and relates the surface images to target position. Both types of optical tracking systems are noninvasive and nonionizing.

Body marker-based optical tracking systems have been widely used for initial patient localization as well as for patient monitoring because of their high spatial resolution, real-time measurement and ease of implementation.

Ambiguity occurs when two cameras are coplanar with two true markers, and the cameras see four markers (two true markers and two ambiguous markers). When an ambiguous marker is present, all known body marker-based optical tracking systems fail to capture (reset zero after CBCT shifts). As a result, a time consuming trial and error process must then be used to remove one of the two true markers that caused the ambiguous marker. Additionally, a reduction in number of true markers for any reason, including the removal of a true marker to eliminate the ambiguous marker, degrades accuracy.

Several known commercially-available, marker-based, optical tracking systems have been developed for the use in radiation therapy.

The first known system, RadioCamera™ (ZMed/Varian, Inc., Ashland, Mass.), uses two ceiling-mounted charge-coupled device (CCD) infrared cameras to detect four passively reflective markers rigidly affixed to a reference array ("biteplate") that links to maxillary dentition of the patient. There are at least two factors limiting use of the first known system in the treatment of lesions in areas such as thoracic and abdominopelvic region: 1) the first known system is specifically designed for the treatment of intracranial lesion and requires the patient to bite a biteplate, and 2) the first known system tracks a rigid, pre-defined marker pattern which disallows a user from choosing other marker patterns.

A second known commercially available optical tracking system, ExacTrac® (BrainLab AG, Munich, Germany), uses two ceiling-mounted CCD infrared cameras to track passively reflective markers. The second known system is designed to track non-rigid body markers affixed directly on the patient's skin. Patient positioning with the second known system has been reported to significantly improve overall setup accuracy at various treatment sites such as head and neck, lung, prostate and pelvic. The second known system is used for initial patient positioning as well as real-time monitoring for SBRT patients treating lung and liver lesions. Treatment flow begins with a CT simulation where six (6) to eight (8) IR markers are affixed to a patient's chest and abdominal region in an irregular pattern. Locations of IR markers and their relationship with respect to the treatment isocenter are semi-automatically identified with software. At a time of treatment, the patient is pre-positioned with the guidance of the second known system. Then, a CBCT scan is acquired with an x-ray volume imaging (XVI) system. A CT to CBCT registration is performed to correct residual target displacement. Isocenter shifts in the second known system need to be reset before continuous monitoring starts. To do this, the second known system captures current marker positions for tracking. Treatment can be interrupted when patient displacement exceeds predetermined tolerances. In such cases, the second known system provides a quick way to reposition patient without additional x-ray imaging. However, the second known system suffers from the ambiguous markers problem and may fail to capture the marker positions. Two ambiguous markers appear when two real markers fall in a same plane as the two CCD cameras. This phenomenon leads to a system failure in capturing new marker positions and consequently, a significant delay in patient treatment. It has been reported that the second known system failed to unambiguously recognize marker patterns in 21% of the fractions for prostate treatment, resulting in an inability to position the patient with the camera. It has also been reported that ambiguity was possible when more than five markers were used. For this reason, with the second known system, it has been reported that the number of external markers should be limited to five, although more markers has been deemed desirable in a study on a correlation between external markers and internal target. The second known system is used for various treatment sites including thoracic and abdominopelvic regions. Its accuracy has been proven for pre-treatment setup and real-time monitoring. However, the second known system suffers from ambiguous markers which limits flexibility in marker placement at CT simulation and leads to significant delay in patient treatment. When two markers are placed in the same plane as cameras, two ambiguous markers are created and the second known system disadvantageously cannot recognize the marker pattern for tracking.

A third known commercially-available, marker-based, optical tracking system is AlignRT® system (Vision RT Limited, London, UK). A fourth known commercially-available, marker-based, optical tracking system is the Real-time Position Management™ system (Varian Medical Systems, Inc., Palo Alto, Calif.).

All known, commercially-available, body marker-based optical tracking systems suffer from an ambiguous markers problem.

In an attempt to establish a one-to-one correspondence between reference markers and optical markers without manual marker labeling, one known method is based on 2D specificity of a marker disposition model. In such known method, all marker positions are projected onto the 2D plane of cameras for classification. This known method has two constraints: 1) missing markers or phantom markers are not allowed; and 2) patient motion must not alter the 2D geometrical peculiarities of the marker disposition model.

SUMMARY OF THE INVENTION

In one embodiment, a computer-implemented method of optically determining location and orientation of an object is disclosed. The method comprises providing a position sensor, including two cameras and an illuminator for emitting infrared light. The method also comprises determining coordinators of each of the two cameras; placing a plurality of retro-reflective markers on an object; creating a set of optical markers, and assigning coordinators to each optical marker, based on infrared light reflected by the retro-reflective markers and received by the position sensor; forming every combination of three optical markers from the set of optical markers; and, for each combination, determining if all three optical markers are in a same plane as the two cameras. The method also comprises, for each optical marker in each same-plane combination, determining whether an optical marker is in the vicinity of the other two optical markers, and, if so, determining whether such optical marker is one of: closer to the two cameras than both of the other optical markers, and farther from the two cameras than both of the other optical markers, and, if so, identifying such optical marker as an ambiguous marker, and removing the ambiguous marker from the set of optical markers whereby the remaining optical markers form a set of true optical markers. The method further comprises determining position and orientation of the object from the set of true optical markers.

In another embodiment, a method of corresponding a set of reference markers $[A_i]$ from a CT scan to a set of optical markers $[B_j]$ detected by cameras in a radiation treatment room is disclosed. The method comprises placing retro-reflective markers on a patient; performing a CT scan of the patient and the retro-reflective markers; assigning x, y, z coordinates to each reference marker of a set of reference markers that appears in the CT scan; determining a distance between each reference markers and each of the other reference markers; viewing the patient and the retro-reflective markers, with cameras in a radiation treatment room; assigning x, y, z coordinates to each optical marker of a set of optical markers created as a result of the viewing; determining a distance between each optical marker and each of the other optical markers; calculating an error function $E=\Sigma_{i=1}^{N-1}\Sigma_{j=2}^{N}\|d_A(i,j)-d_B(C(i), C(j))\|^2$ in an iterative fashion, where $d_A(i,j)$ denotes distance between two reference markers of the set of reference markers $[A_i]$, $d_B(i,j)$ denotes distance between two optical markers of the set of optical markers $[B_j]$, C is a mapping function that defines an index of an optical marker that corresponds to a reference marker, and N is a number of markers that are mapped; and determining a maximum N that minimizes E, subject to: $E \leq \delta$, and $\|d_A(i,j)-d_B(C(i), C(j))\| \leq \epsilon$, $\forall$ i, j $\in$ A, where $\delta$ and $\epsilon$ depend on one or more of: CT spatial resolution, CT noise, camera noise, magnitude of motion of the patient near the markers, number of markers, and reproducibility of placement of the markers on the patient.

BRIEF DESCRIPTION OF THE DRAWINGS

The accompanying Figures, in which like reference numerals refer to identical or functionally similar elements throughout the separate views and which together with the detailed description below are incorporated in and form part of the specification, serve to further illustrate various embodiments and to explain various principles and advantages all in accordance with the present invention, in which.

DETAILED DESCRIPTION

As required, detailed embodiments of the present invention are disclosed herein. However, it is to be understood that the disclosed embodiments are merely examples of the invention, which can be embodied in various forms. Therefore, specific structural and functional details disclosed herein are not to be interpreted as limiting, but merely as a basis for the claims and as a representative basis for teaching one skilled in the art to variously employ the present invention in any appropriately detailed structure and function. Furthermore, the terms and phrases used herein are not intended to be limiting; but rather, to provide an understandable description of the invention.

Figure 1:
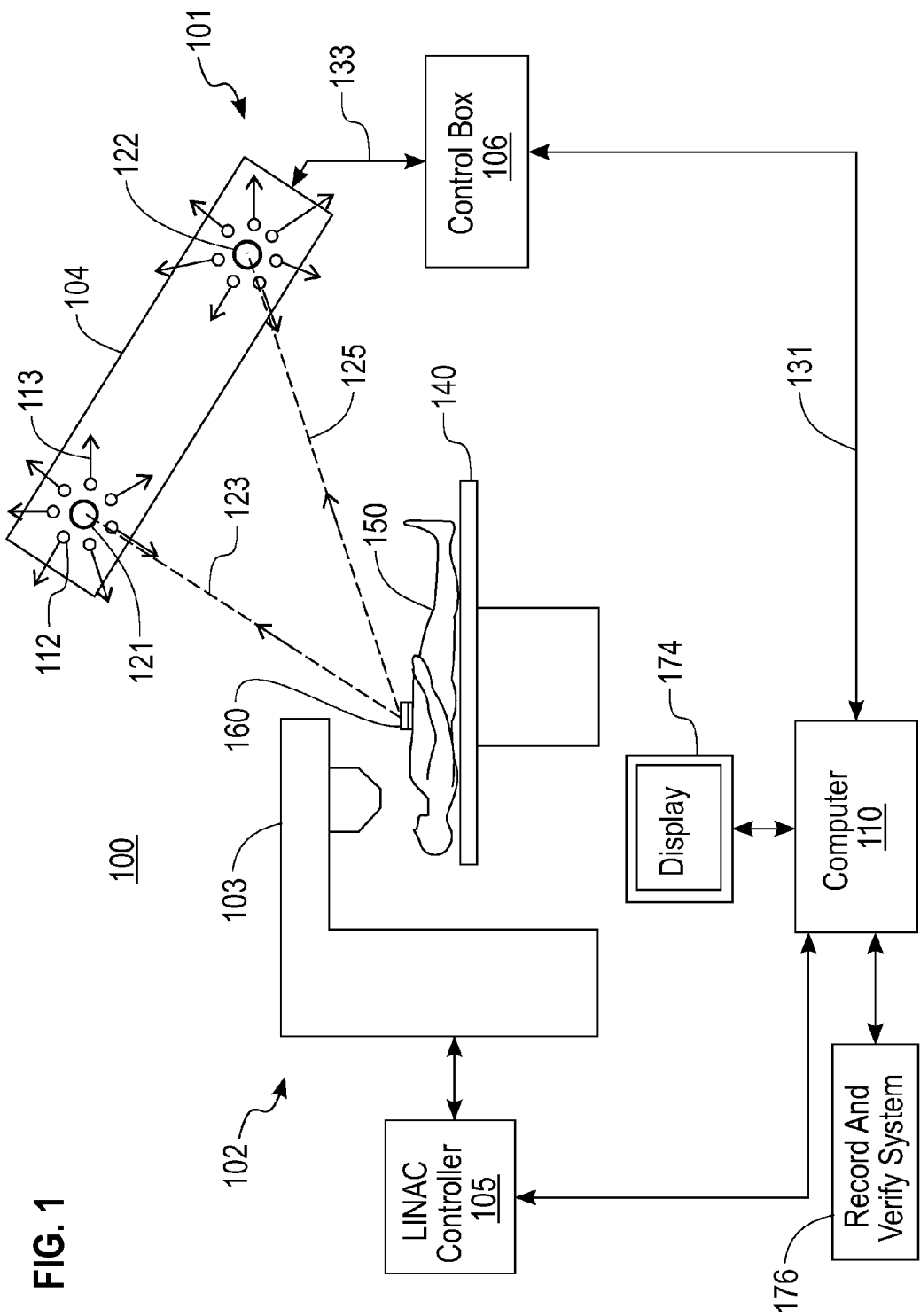
FIG. 1 is a simplified block diagram of an ambiguity-free optical tracking system in accordance with one embodiment of the invention, and a radiation delivery system.

FIG. 1 is a simplified block diagram of one embodiment of an ambiguity-free optical tracking system 101 in accordance with the invention, and a radiation delivery system 102. The ambiguity-free optical tracking system 101 is ambiguity-free because it automatically identifies and eliminates ambiguous markers. The radiation delivery system 102 is a conventional system except as noted hereinbelow. In one embodiment, the radiation delivery system 102 includes a dual energy linear accelerator (hereinafter "LINAC") 103 for performing external beam radiotherapy and a controller 105 for controlling the LINAC.

The ambiguity-free optical tracking system (hereinafter "optical tracking system") 101 comprises a position sensor unit 104, a control box 106, a computer 110, such as a personal computer, and software. The position sensor unit 104 is mounted on a ceiling of the treatment room. The position sensor unit 106 includes one or more illuminators 112 for emitting infrared (IR) light as indicated by arrows 113, and two charge-coupled device cameras (hereinafter "cameras") 121 and 122 for receiving reflected IR light as indicated by dotted lines 123 and 125. In one embodiment, the optical tracking system 101 uses a Polaris® position sensor unit by Northern Digital, Inc., of Waterloo, Ontario. In one embodiment, the computer 110 is located in a LINAC treatment room (hereinafter "treatment room"). Software residing in the computer 110 communicates with the control box 106 of the optical tracking system 101. The software comprises computer program instructions, or code, for executing the ambiguity elimination algorithm, for executing the backtracking algorithm, and for communicating with the control box 106. The computer 110 is connected to the control box 106 through a serial cable 131. The control box 106 is connected to the position sensor unit 104 through a proprietary cable 133.

The radiation delivery system 102 includes a treatment couch (hereinafter "couch") 140. A patient 150, who is undergoing radiation treatment, or radiotherapy, is shown lying on the couch 140. With the optical tracking system 101, a plurality of specially-designed retro-reflective, or infra-red reflective, markers 160 are affixed on a surface of the patient 150. The position sensor unit 104 is mounted above a foot of the couch 140. In one embodiment, the two cameras 121 and 122 of the position sensor unit 104 are 50 cm apart. Real-time position of each marker 160 is captured approximately fifteen (15) frames per second, i.e., 15 Hz, by the cameras 121 and 122. An internal processing unit (not shown) of the position sensor unit 104 performs triangulation, based on IR light reflections from each marker 160 and received by the cameras 121 and 122 which act as sensors. The optical tracking system 101 simultaneously tracks multiple markers affixed on the patient's skin or on an immobilization device. The position sensor unit 104 determines three-dimensional (3D) coordinates of each marker 160 in a native coordinate system of the optical tracking system 101, and sends the 3D coordinates to the computer 110. Three-dimensional (3D) coordinates of up to fifty (50) markers can be sent back to the computer 110 at a same time. The control box 106 of the optical tracking system 101 works in passive mode, i.e., it responds to each command (e.g., initialize the cameras 121 and 122; read location of each marker 160; close the connection, etc.) sent from the computer 110 but the control box does not initiate any communication.

For simplicity of illustration, FIG. 1 shows IR light reflections from only one marker 160. It should be understood that the optical tracking system 101 is used when there are a plurality of markers on the patient 150 (see FIGS. 3, 6, 9 and 13). It should be understood that each marker 160 of such plurality of markers on the patient 150 independently reflects light back to the position sensor unit 104 based on a respective location of each marker on the patient. Based upon relationship(s) between and among location of each marker 160 of such plurality of markers, ambiguous markers may be detected by the position sensor unit 104 using IR light reflections from the real markers. Of course, ambiguous markers are not physical markers; therefore, ambiguous markers do not, and cannot, reflect any light. Confirmation that the position sensor unit 104 detected one or more ambiguous markers can be immediately determined if a number of markers outputted by the control box 104 exceeds a number of markers on the patient 150. However, the output from the control box 106 does not identify which marker(s) is/are ambiguous and which markers are real.

Inquiries and requests from the computer 110 are sent to the control box 106, and the control box responds with a list of coordinates of each marker 160 in a camera native coordinate system. Some of the markers 160 on such list may be ambiguous markers. A calibration procedure, described hereinbelow, is designed to transform the coordinate system from the camera native coordinate system to a coordinate system of the LINAC 103. Then, a pattern matching subroutine is executed to find a correspondence between optical markers and reference markers. Rotation and shift corrections for patient setup are computed between corresponding markers with a general analytical method using singular value decomposition (SVD), as described herein below. Advantageously, the ambiguous markers on such list are automatically identified and eliminated by the optical tracking system 101, as explained more fully hereinbelow.

Figure 2:
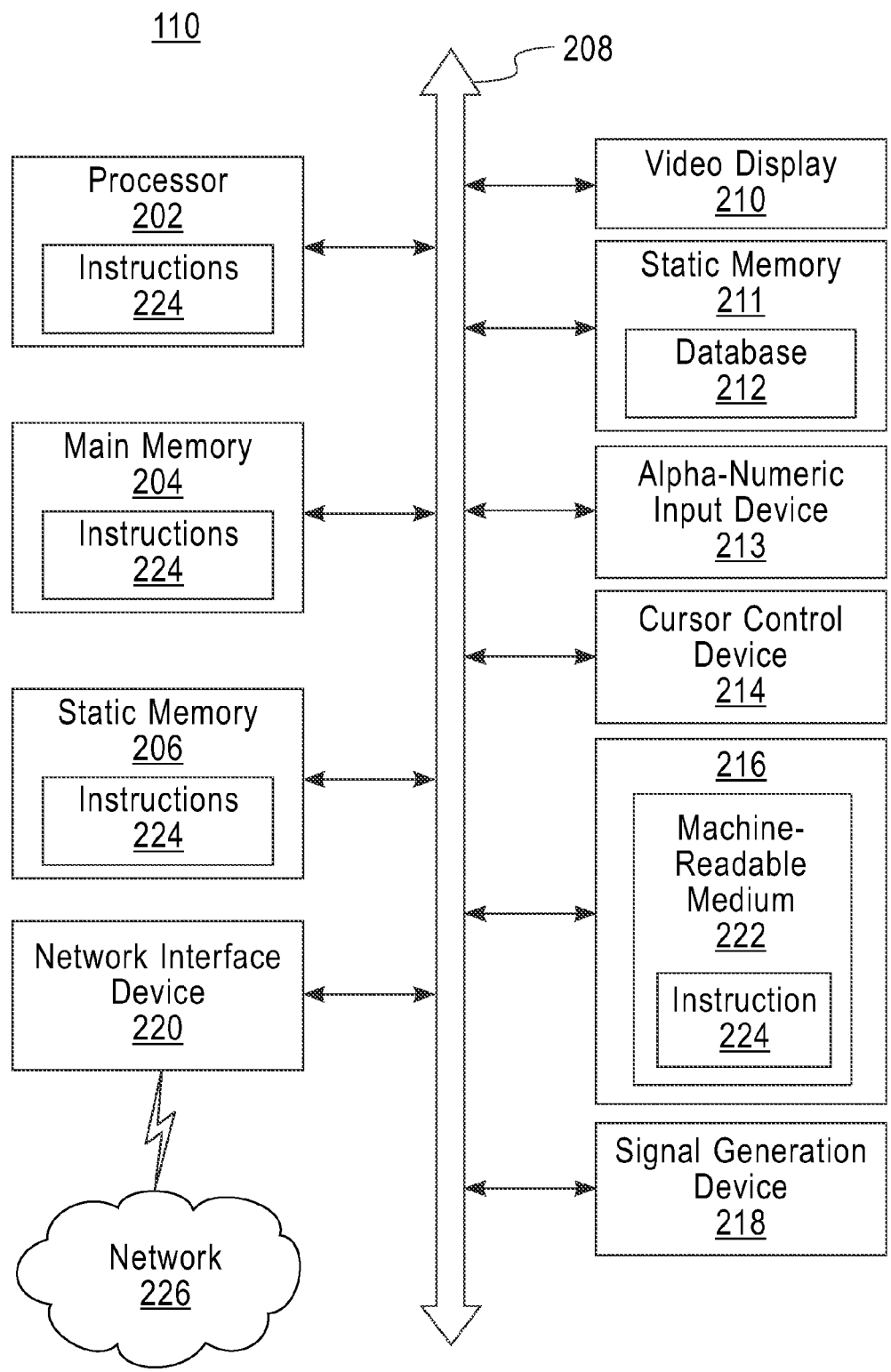
FIG. 2 is a simplified block diagram of one embodiment of the computer shown in FIG. 1.

FIG. 2 is a simplified block diagram of the computer 110. The computer 110 may include a processor 202 (e.g., a central processing unit (CPU), a graphics processing unit (GPU) or both; a main memory 204 such as random access memory (RAM); and a static memory 206, such as read-only memory (ROM) or a hard disk, that holds instructions, which communicate with each other via a bus 208. The bus 208 is connected to a display controller 210 which is coupled to the display 174 such as a liquid crystal display (LCD). The display 174 is used to show, or present, information about the computer 110. The computer 110 may also include another static memory 211, such as a hard disk, that holds a database (DB) 212; an input device 213 such as a keyboard; a cursor control device 214 such as a mouse or a trackpad; a memory device 216 such as disk drive unit or solid state memory, a signal generation device 218 such as a speaker or audible alarm; and a network interface device 220, which are coupled to the bus 208. The disk drive unit 216 may include a tangible computer-readable storage medium 222 on which is stored one or more sets of instructions 224 (i.e., software) embodying any one or more of the methods or functions described herein, including those methods illustrated herein. The instructions 224 may also reside, completely or at least partially, within the main memory 204, the static memory 206, and/or within the processor 202 during execution thereof by the computer 110. A set of instructions 224, when executed, may cause the computer 110 to perform any one or more of the methods discussed herein. The main memory 204 and the processor 202 also may constitute non-transitory tangible computer-readable storage media. Although only one CPU 202 is illustrated for computer 110, a computer with multiple CPUs can be used equally effectively.

Embodiments of the present invention also incorporate interfaces that each includes separate, fully programmed microprocessors that are used to off-load processing from the CPU 202. An operating system (not shown) included in the main memory is a suitable multitasking operating system such as any of the Linux, UNIX, Windows, and Windows Server based operating systems. Embodiments of the present invention are able to use any other suitable operating system. Some embodiments of the present invention utilize architectures, such as an object oriented framework mechanism, that allows instructions of the components of operating system (not shown) to be executed on any processor located within the information processing system. The bus 208 is also connected to a communication controller that conforms to, for example, an Ethernet protocol. The communication controller may be used to physically connect the computer 110 with a network. The network adapter hardware 220 is used to provide an interface to a network 226 as illustrated. Embodiments of the present invention are able to be adapted to work with any data communications connections including present day analog and/or digital techniques or via a future networking mechanism. Although the tangible computer-readable storage medium 222 is shown in an example embodiment to be a single medium, the term "tangible computer-readable storage medium" should be taken to include a single medium or multiple media (e.g., a centralized or distributed database, and/or associated caches and servers) that store the one or more sets of instructions. The term "tangible computer-readable storage medium" shall also be taken to include any non-transitory medium that is capable of storing or encoding a set of instructions for execution by the computer and that cause the computer to perform any one of the methods discussed herein.

Camera Calibration

A calibration procedure transforms the 3D coordinates from the camera native coordinate system to an absolute room coordinate system. Calibration of the cameras utilizes a calibration jig that places m passive markers at known coordinates relative to machine isocenter. The coordinates of these markers are collected into an m×3 matrix A. The calibration jig is accurately positioned to machine isocenter with the guidance of the CBCT. The coordinates of the optical markers in the camera's native coordinate system are optically sampled n times by the cameras. Averages are collected into another m×3 matrix B:

$$A, B = \begin{pmatrix} x_1 & y_1 & z_1 \\ \vdots & \vdots & \vdots \\ x_m & y_m & z_m \end{pmatrix}$$

An objective of the calibration is to find a rotation matrix R and a translation matrix T, such that $$A = BR + T.$$

The marker coordinates A and B are respectively measured with CT and optical cameras and so they are subject to noise. The optimal solution of R and T can be found by a least-squares estimation that minimizes the following expression:

$$\epsilon^2 = \|A - BR - T\|.$$

This is known as the relative pose problem in computer vision language. There are three basic solutions to the relative pose problem 1) an exact closed-form solution for three markers, 2) a solution via SVD for four or more markers, and 3) an iterative solution for at least three markers. It has been shown that all three solutions yield the same result when properly implemented. For a general analytical solution via SVD, the steps are summarized as follows. 1) Centroids ($A_c$) and ($B_c$) are subtracted from A and B, respectively to offset the origin of both coordinate systems and remove the translation from A to B. 2) The SVD of $B^T A$ is computed as $$B^T A = U W V^T,$$

where U and V are unitary matrices and W is a diagonal matrix whose diagonal entries are equal to the singular values of $B^T A$. 3) The solutions of R and T are given as $$R = U \begin{pmatrix} 1 & 0 & 0 \\ 0 & 1 & 0 \\ 0 & 0 & \det(UV^T) \end{pmatrix} V^T,$$

and $$T = A_c - B_c R.$$

There are two approaches to eliminate ambiguous markers. One approach is by using the backtracking algorithm to match a reference marker array (which, by definition, has no ambiguities) with a detected marker array. Another approach is by using the ambiguity elimination algorithm.

In circumstances where a reference marker array is available (e.g., from a CT simulation scan and defined in TPS), a one-to-one correspondence can be established between each reference marker and a true marker by using the backtracking algorithm. Any unmatched markers in the detected marker array are, therefore, ambiguous markers and they will not be considered in any subsequent calculation.

When a reference marker array is not available, e.g., no markers affixed on the patient in CT simulation, but there are markers applied during treatment, the ambiguity elimination algorithm is used. Based on geometry of markers in a detected marker set, the ambiguity elimination algorithm identifies which markers are ambiguous markers and the ambiguity elimination algorithm eliminates the ambiguous markers from any further consideration.

Automatic Ambiguity Elimination

Figure 3:
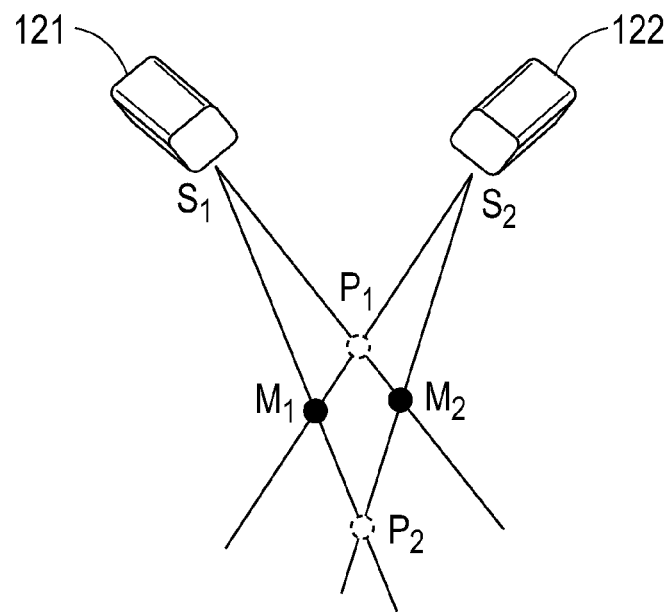
FIG. 3 illustrates an example of a cause of ambiguous markers.

FIG. 3 illustrates an example of a cause of ambiguous markers. Two true markers $M_1$ and $M_2$ lie in a same plane as the two cameras $S_1$ and $S_2$. The cameras receive reflected IR light from each true marker (represented by virtual lines connecting sensor to the true markers). Intersections of virtual lines originating from $S_1$ and $S_2$ define four possible marker positions: two true markers $M_1$ and $M_2$, and two ambiguous markers $P_1$ and $P_2$. A cause of ambiguous markers can be explained by a principle of marker detection by a camera system illustrated in FIG. 3. A camera, which acts as a sensor, intercepts IR light reflected from the marker and establishes a virtual line connecting itself to the marker. A second camera determines another virtual line between itself and the same marker. An intersection of these two virtual lines is regarded as the marker location, and its 3D coordinates are determined through a process called triangulation. In case two markers ($M_1$ and $M_2$ in FIG. 3) lie in a same plane as the two cameras ($S_1$ and $S_2$), each camera determines two virtual lines as shown in FIG. 3. These two pairs of virtual lines create four possible intersections for potential marker positions: real markers $M_1$ and $M_2$, and ambiguous markers $P_1$ and $P_2$. The camera cannot distinguish between true markers and ambiguous markers and the camera reports back the 3D coordinates of all four intersections. The ambiguity elimination algorithm automatically eliminates ambiguous markers through a post-process method.

First, the 3D coordinates of the cameras in camera's native coordinate system are determined as part of the calibration procedure. All but two of the markers on the calibration jig are blocked, such as by using caps made of paper. A graphical user interface (GUI) based on OpenGL® (Silicon Graphics International Corp., Fremont, Calif.) shows all marker positions reported by the camera in real time. The calibration jig is rotated and shifted such that the two exposed markers fall on the same plane as the two cameras. This is achieved by placing the two markers parallel to the cameras. When the two exposed markers fall on the same plane as the two cameras, four markers are observed on the GUI instead of two, as shown in FIG. 3. The 3D coordinates of the four markers are captured and saved for post processing. Connecting each two of the four markers gives six (6) line segments. Only two of them (diagonals) cross each other and they are easy to identify. It is trivial to show that one of the two diagonal line segments joins the two true markers, and the other of the two diagonal line segments joins the two ambiguous markers. If the endpoints of one diagonal line segment are connected to the endpoints of the other diagonal line segment and the lines are extended, their intersections determine a position of each camera. In FIG. 3, the two diagonal line segments that cross each other are $M_1M_2$ and $P_1P_2$. The sensor positions $S_1$ and $S_2$ are determined as the intersection of lines $P_2M_1$ and $M_2P_1$ and by the intersection of lines $M_1P_1$ and $P_2M_2$, respectively.

Ambiguous marker elimination is performed in the camera's native coordinate system; therefore, the ambiguous marker elimination is independent of the camera calibration (matrices R and T). It is not necessary to determine the position of each camera every time such camera is recalibrated. Formation of ambiguous markers ($P_1$ and $P_2$ in FIG. 3) involves two true markers ($M_1$ and $M_2$) and they need to fall on the same plane as the two cameras ($S_1$ and $S_2$). For convenience, each point (sensors or markers) in FIG. 3 is regarded as a vector in 3D space and defines a variable $\lambda$ which determines the location of a point on a line segment. For example, two ways to describe the intersection $P_1$ of two line segments $S_1M_2$ and $S_2M_1$ are:

$$P_1 = S_1 + \lambda_{S_1}(M_2 - S_1) \text{ and}$$

$$P_1 = S_2 + \lambda_{S_2}(M_1 - S_2),$$

where $\lambda_{S_l}$ (l=1 or 2) defines the relative location of a point on the line segment connecting sensor $S_l$ and a marker. Values of $\lambda$ range from negative to positive infinity. Only points with a positive $\lambda$ are considered. The value of $\lambda$ is less than one when a point falls between the sensor and the marker, and the value of $\lambda$ greater than one when a point is away from the sensor and beyond the marker. An ambiguous marker is either closer to or farther from the cameras than both true markers. In this example, ambiguity $P_1$ is closer to the cameras than both true markers which makes $\lambda_{S_1}$ and $\lambda_{S_2}$ both less than one simultaneously; ambiguity $P_2$ is farther from the cameras than both true markers which makes $\lambda_{S_1}$ and $\lambda_{S_2}$ greater than one at the same time. This is the basis of the ambiguity elimination algorithm. The ambiguity elimination algorithm picks up three markers from a list each time and checks if they lie in a same plane as both sensors. If three markers pass a coplanar check, one of them is identified as an ambiguity if 1) it falls in the vicinity of the intersection of two lines, with one line connecting one sensor and one of the two remaining markers and, the other line connecting the other sensor and the other remaining marker, and 2) $\lambda_{S_1}$ and $\lambda_{S_2}$ are simultaneously less than or greater than one. The ambiguous marker is removed from the list and this process repeats until no more ambiguous markers can be identified.

Marker Correspondence

A correspondence between reference markers and optical markers need to be decided before patient pose can be estimated with the closed form general analytical solution. A marker list sent back from the camera does not follow a particular order; therefore, a one-to-one relationship cannot establish automatically. The backtracking algorithm efficiently establishes the correspondence between points from two marker sets. The backtracking algorithm effectively deals with missing, misplaced and occluded markers.

The problem is formulated mathematically as follows. Assume there are two sets of 3D markers, a set $[A_i]$ from reference CT images and a set $[B_j]$ from the camera. The sets are related by a rigid transformation-rotation R and translation T. The pose problem—solving for R and T—can be solved after the establishment of marker correspondence and will be discussed in the registration with reference data section hereinbelow. Number of markers clinically used may range from four (4) to nine (9). The positions of the markers are measured with CT or the camera, and are subject to noise. It is also possible to have misplaced or missing markers in $[B_j]$ because the tattoos on the patient's skin for marker placement may not be identified accurately or completely. Some markers may be occluded from the camera(s) due to slope of patient's skin surface. Therefore, outliers may be present in either set of markers, and the number of markers in the set $[A_i]$ from reference CT images may not be identical to the number of markers in the set $[B_j]$ from the camera. $d_A(i,j)$ and $d_B(i,j)$ are used to denote the Euclidean distance between marker A(i) and A(j) and markers B(i) and B(j), respectively. A correspondence function C(i) defines an index of the marker in set B that corresponds to marker A(i). Due to potential misplaced or missing markers, C(•) may only map a subset of set A to a subset of set B. A size of the subset is denoted by N. An error measure defined on the subset is given by $$E = \sum_{i=1}^{N-1} \sum_{j=2}^{N} \|d_A(i,j) - d_B(C(i), C(j))\|^2$$

The error measure is based on the principle of invariance of distance under rigid transformation and it excludes points in set A which do not have corresponding points in set B. A problem can be formulated to find a maximum subset $A_s$ of set A, and a one-to-one correspondence function C(•) defined on the subset, which minimize E subject to:

$$E \leq \delta, \text{ and}$$

$$\|d_A(i,j) - d_B(C(i),C(j))\| \leq \epsilon, \forall i,j \in A_s$$

The choice of threshold $\delta$ and $\epsilon$ depends on factors such as CT spatial resolution, CT and optical camera noise, magnitude of patient motion where markers are affixed, number of markers, and reproducibility of marker placement.

Figure 4:
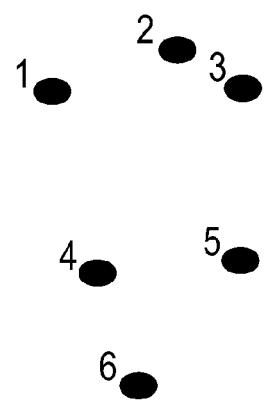
FIG. 4 illustrates an example of conditions wherein a backtracking algorithm may be used.
Figure 4:
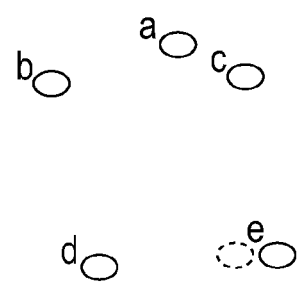

FIG. 4 illustrates an example of conditions wherein a backtracking algorithm may be used. A sought one-to-one correspondence between reference marker set A and optical marker set B is [(1, b), (2, a), (3, c), (4, d), (5, e)]. For demonstration purpose: order of markers a and b in set B is switched, no marker in set B corresponds to marker "6" in A, and marker e is slightly misplaced. The following is a description of the backtracking algorithm that can handle misplaced or missing markers. In this example, there are six markers in the reference marker set A and five markers in the optical marker set B, given in 3D coordinates in no particular order. Without loss of generality, the markers in set A are labeled as "1" through "6", and the markers in set B are labeled as "a" through "e". The correspondence sought between the two sets is given by the pairing [(1, b), (2, a), (3, c), (4, d), (5, e)]. For demonstration purposes, the order of markers a and b are intentionally switched. No marker in set B corresponds to marker 6 in set A which simulates a missing or occluded marker. As an example, marker e in set B is slightly misplaced. An exhaustive recursion approach would attempt each permutation of the markers in set B and check if it satisfies the two constraints defined above. The exhaustive recursion approach is not efficient but it guarantees to find an optimal solution if there are no outliers such as missing or significantly misplaced markers. To deal with outliers, the concept of null markers is utilized. A null marker is added to match a marker in set A when it is suspected there is no marker in set B to match the marker in set A. A structured approach utilizing a backtracking technique is used to search for an optimal solution. Backtracking incrementally builds candidates to the solutions, but quickly abandons most partial solutions based on the constraints in the problem which makes it more efficient than the exhaustive recursion approach.

Figure 5:
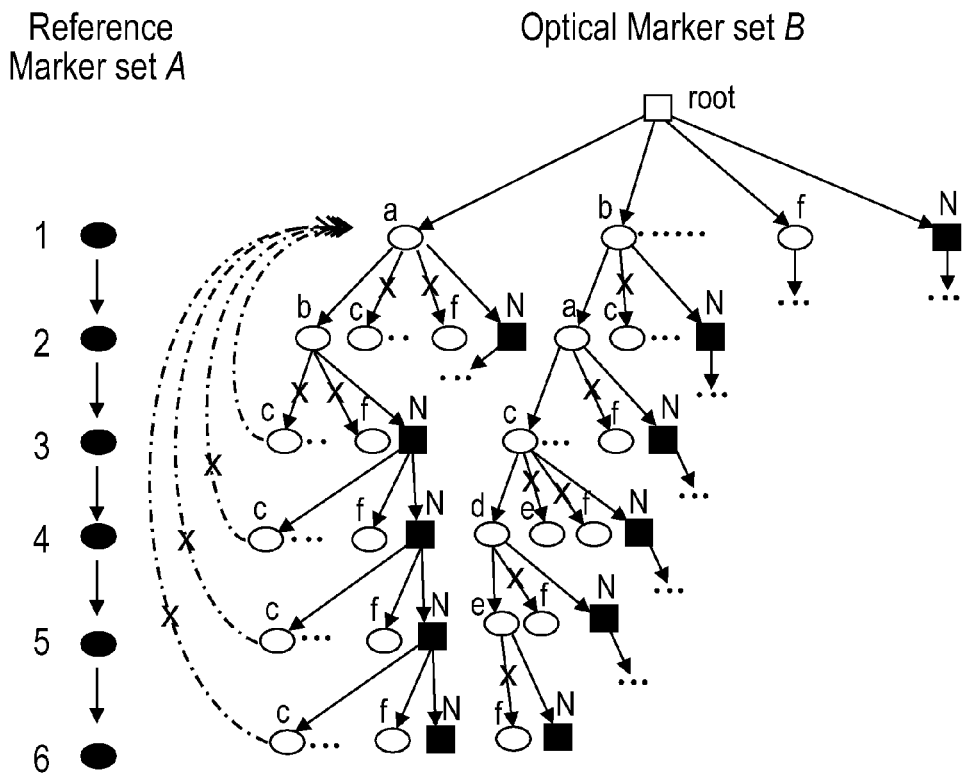
FIG. 5 illustrates an example of operational steps of the backtracking algorithm.

FIG. 5 illustrates an example of operational steps of the backtracking algorithm. Markers in set B are attempted to match markers in set A one at a time. Distance constraint is checked at each level and overall error measure is checked for a complete solution. Optimal solution is a solution with a maximum number of matching markers and a least error measure. Null markers are introduced to deal with missing or occluded markers. Markers in set A are listed on the left. Nodes of the recursive tree (except the root node) on the right represent either markers from set B or null markers. Nodes on a same level of the tree potentially match the marker in set A at the same level. Starting with level one $L_1$, each marker in set B could be assigned to match marker 1 in A without prior knowledge. It is also possible that no corresponding marker in set B matches marker 1, so a null node (labeled as "N") is introduced. A likelihood of each case is checked and a subtree is constructed with one of the markers or a null node as its root. At lower level $L_n$ (n=2 . . . 6), each remaining candidate marker $B_r$ in set B is attempted with a feasibility checked with two distances between markers: 1) a distance between $B_r$ and its parent marker (indicated by downwards arrows between adjacent levels), and 2) a distance between $B_r$ and the root marker at $L_1$ of the corresponding subtree (indicated by upwards dashed arrow between $L_n$ and $L_1$). As part of the second constraint, these two distances are compared with the corresponding distances in set A. The current solution is abandoned if the difference of either distance exceeds a A distance check passes automatically if a null node is involved. A search proceeds in a depth-first fashion and backtracking happens when a partial solution is abandoned or the search hits the bottom level of the tree. A search path successfully reaching the bottom level of the tree constructs a potential valid solution. The error measure along such path is computed and compared with δ if it constitutes no fewer non-null markers than the currently found best solutions. The final solution is the one with a maximum number of markers and the error measure within δ. In this example, (a, b, N, N, N, N) and (b, a, c, d, e, N) are two of the valid solutions to match (1, 2, 3, 4, 5, 6). But the second one has the most matching markers and it is the solution that is sought. The backtracking algorithm acts as a marker correspondence algorithm.

Registration with Reference Data

Figure 6:
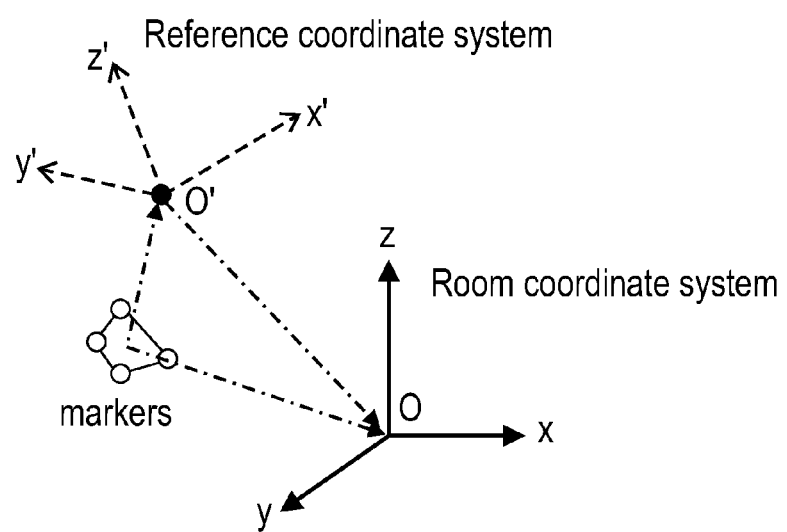
FIG. 6 illustrates an example of registration of patient orientation and position.

FIG. 6 illustrates an example of registration of patient orientation and position wherein there are four (4) markers on a patient, such as the patient 140. Registration of patient orientation and position is performed by aligning two coordinate systems. The reference coordinate system is defined from a CT image set, with tumor center as its origin. Center of the room coordinate system is located at machine isocenter. The registration aligns patient orientation to treatment orientation and brings tumor center to machine isocenter. In the optical tracking system, patient position and orientation is estimated through rigid registration of optical marker sets to reference marker sets. In reference marker sets, the 3D coordinates of markers are given with respect to tumor center. In optical marker sets, coordinates of markers are obtained in camera native coordinate system and converted to room coordinate system via the calibration procedure described in the camera calibration section hereinabove. As shown in FIG. 6, the origin of the reference coordinate system x' y' z' and the room coordinate system xyz are located at a center of a tumor O' and machine isocenter O, respectively. The rigid registration calculates necessary rotation and shift to align patient position and orientation as planned. As a result, the center of the tumor moves to the machine isocenter.

The registration process shares similarities with the calibration process, discussed above, in the sense that each of them deals with alignment of two coordinate systems. A difference is as follows. In the calibration process, one coordinate system (the camera native coordinate system) is converted to the reference coordinate system. In the registration system, the reference coordinate system is converted to another coordinate system (a room coordinate system observed by camera but converted via calibration matrices). Therefore, if reference markers and optical markers are collected into matrix B and A, respectively, (roles of matrix A and B are exchanged compared to the calibration process), the rotation R and shift T to align the patient can be calculated with exactly a same solution outlined hereinabove regarding camera calibration. Before the calculation, ambiguities in the optical marker set are eliminated in the camera native coordinate system, and marker correspondence is established, as described hereinabove regarding automatic ambiguity elimination, and marker correspondence, respectively.

Synergy with a Record and Verify System

A pattern of reference markers applied to a same treatment site for different patients may appear similar. To maximize patient safety in radiotherapy and to ensure the right reference marker set is loaded for the right patient, the optical tracking system works in synergy with a record and verify (R&V) system. An example of a R&V system is MOSAIQ® 2.30 (Elekta, Inc., Sunnyvale, Calif.). When a new patient is loaded in the R&V system, the optical tracking system automatically pre-loads the matching patient's reference data to eliminate any chance of using another patient's data, i.e., a wrong patient's data, for optical guidance. When a patient's treatment or setup field is loaded in MOSAIQ, a temporary file containing patient information such as patient name and medical record number is created at a common network folder. The optical tracking system constantly monitors this file and automatically loads in the patient's reference marker set while prompting the user to confirm. The optical tracking system does not proceed until its patient information matches information of the patient currently loaded in MOSAIQ.

The camera system works in synergy with the R&V system to maximize patient safety in radiotherapy. The camera system constantly monitors the patient loaded in R&V and is able to automatically load the right reference marker sets. This unique feature, which is not available in commercial optical tracking systems, is of critical importance in ensuring patient safety. Patients treating the same area could share the same marker pattern. The integration of the camera system and R&V system can effectively eliminate the possibility of using wrong patient's data for localization or monitoring.

System Evaluation

Experiments have been designed to evaluate the accuracy of the optical tracking system. The accuracy of calibration and registration of the optical tracking system was evaluated independently against CBCT as well as against the second known system which was installed side-by-side with the optical tracking system. The effect of number of markers on calibration and registration accuracy was also evaluated. Finally, its performance in eliminating ambiguities was assessed.

System Calibration Accuracy

An experiment was performed to check the accuracy of calibration of the optical tracking system. The calibration was done with an isocenter phantom. There were five (5) markers installed on the phantom. Coordinates of the center of each marker relative to phantom center were determined through a 1 mm CT scan. During calibration, the phantom was placed to isocenter position by aligning engraved lines on the phantom to room lasers. A CBCT image set of the phantom was acquired with the XVI system and was registered to reference CT to reduce residual errors. An isocenter coincidence of the XVI system and machine megavoltage isocenter was checked right before calibration. The rotation matrix R and the translation matrix T, which convert camera native coordinate system to room coordinate system, were computed following the steps outlined in the camera calibration section hereinabove. The second known system was also calibrated at a same time following vendor-provided guidelines. A pelvis phantom was used to evaluate the accuracy of the calibration. Eight (8) IR markers were affixed to the phantom in a widespread region for CT scan. Marker positions were identified and exported to both the second known system and the optical tracking system as reference data. The phantom was placed in a treatment position under the guidance of the second known system to within ±0.1 mm and ±0.1° along all three axes. Isocenter corrections (translation and rotation) were evaluated with the XVI system as well as the optical tracking system. This test was repeated six times to obtain statistics of the isocenter corrections. Effects of number of markers were also evaluated by gradually reducing number of markers from eight (8) to four (4) during each test. The markers on the peripherals were blocked with paper-made caps one at a time. Mean differences of isocenter corrections of the second known system and the optical tracking system were compared to those of the XVI system as evaluation of system calibration accuracy.

System Registration Accuracy

An experiment was performed to check the accuracy of registration of the optical tracking system. The pelvis phantom was placed to treatment position as determined by the second known system. The residual errors of isocenter corrections of the XVI system, of the second known system, and of the optical tracking system were recorded as baseline. Translational displacements of ±10 mm and ±20 mm and rotational displacements of ±5° were applied to the phantom separately along each axis. Isocenter corrections reported by each system were recorded for comparison. Then, combined translation within ±20 mm and rotation within ±5° were applied to the phantom simultaneously along all three axes. Translational displacement was achieved by shifting the couch 140 while rotational displacement was achieved by rotating the phantom with the help of hand-made wedges. Isocenter corrections of the two optical systems were compared with those of the XVI system in each case. Baseline shifts and rotations were subtracted from each system. Effects of number of markers were evaluated in the same way as described in system calibration accuracy section, hereinabove.

Ambiguity Elimination Accuracy

Automatic ambiguity elimination is a unique feature of the optical tracking system. A synthetic test case and a clinic case were designed to evaluate performance of the optical tracking system. In the synthetic test case, three collinear IR markers, 5-6 cm apart, were mounted on a flat plastic board. The number of markers and the pattern was compared between the two optical tracking systems when the markers were placed parallel to them. The effectiveness of ambiguity elimination by the optical tracking system was assessed by turning on or off the ambiguity elimination feature in the software and observing the difference in markers detected. In the clinic case, a clinically-used pattern of eight (8) IR markers was reproduced on the pelvis phantom. The phantom was positioned such that ambiguous markers showed up in the camera. Then, the ambiguity elimination algorithm was turned on to check whether the ambiguous markers were accurately identified and eliminated in the optical tracking system.

Results

Comparison of difference in system calibration between the optical tracking system and the CBCT and the second (2nd) known system is shown in Table 1.

TABLE 1

| N = 6 | Translation (mm) | | | | Rotation (°) | | |
| --- | --- | --- | --- | --- | --- | --- | --- |
| | LAT | LONG | VERT | VECT | PITCH | ROLL | YAW |
| vs. CBCT | 0.31 ± 0.27 | 0.36 ± 0.23 | 0.26 ± 0.15 | 0.58 ± 0.31 | 0.91 ± 0.21 | 0.63 ± 0.13 | 0.27 ± 0.08 |
| vs. 2nd | 0.35 ± 0.33 | 0.09 ± 0.05 | 0.51 ± 0.19 | 0.69 ± 0.22 | 0.34 ± 0.08 | 0.28 ± 0.04 | 0.14 ± 0.08 |

The pelvis phantom was placed to treatment position with the guidance of the second known system. Detected isocenter displacement was recorded for each system. The experiment was repeated six (6) times. Shown in Table 1 are the mean and one standard deviation of the difference between the optical tracking system versus CBCT and the second known system.

Figure 7:
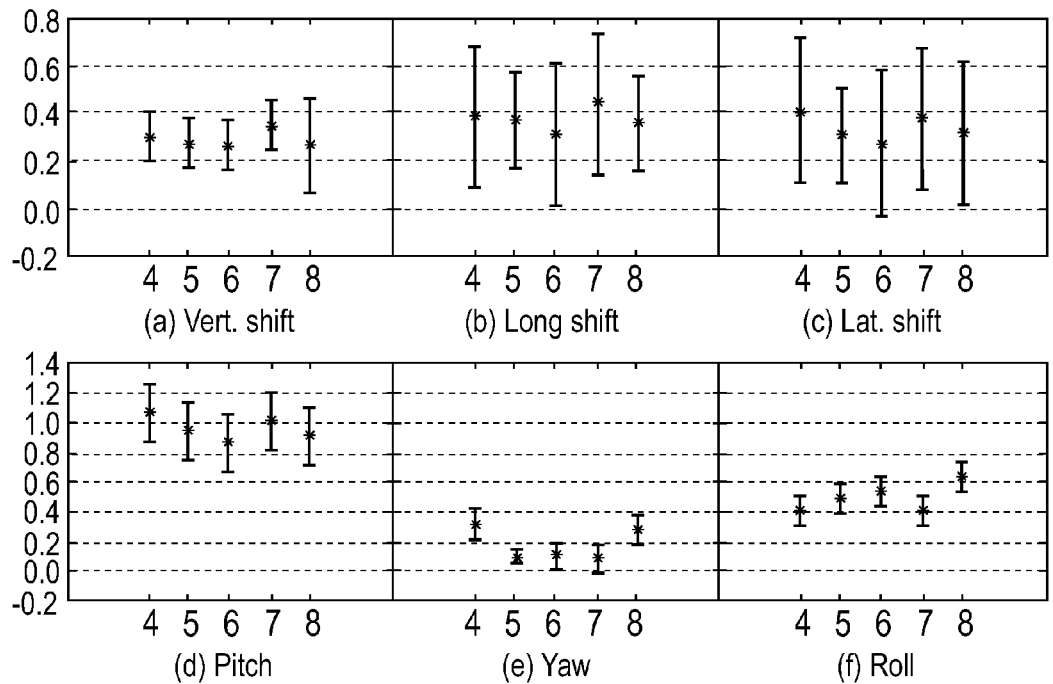
FIG. 7 illustrates effect of number of markers on calibration accuracy of the optical tracking system.

Lateral, longitudinal and vertical translations are along left-right (LR), superior-inferior (SI), and anterior-posterior (AP) axes, respectively. Pitch, roll and yaw rotations are around the three axes, respectively. The mean translation and rotation deviations were within 0.4 mm and 1° when compared to CBCT; the means and standard deviations (SDs) of translation difference were 0.31 mm+0.27 mm, 0.36 mm+0.23 mm, and 0.26 mm+0.15 mm for lateral, longitudinal and vertical axis, respectively. The overall deviation for all three directions combined was 0.58 mm+0.31 mm. The deviations in pitch, roll and yaw rotations were 0.91°±0.21°, 0.63°±0.13°, and 0.27°±0.08°, respectively. When comparing the calibration between the optical tracking system and the second known system, the translational deviation was generally within 0.5 mm; good agreement in rotation was observed with deviation in all three rotations less than 0.5°. The translational deviation was 0.35 mm+0.33 mm, 0.09 mm±0.05 mm, and 0.51 mm+0.19 mm, respectively. The combined shift in all three axes was 0.69 mm+0.22 mm FIG. 7 illustrates an effect of number of markers in a calibration accuracy of the optical tracking system. Shown are differences of detected isocenter displacement in translation (a-c) and rotation (d-f) of the camera system compared to CBCT. The x-axis represents number of markers range from eight (8) to four (4). The y-axis represents difference of shift, in millimeters, in (a-c) and rotation, in degrees, in (d-f). The x-axis represents number of markers ranging from four (4) to eight (8) and the y-axis represents the deviations in translation (a-c) or rotation (d-f). The error bar represents one standard deviation. No clear trend was evident when reducing the number of markers from eight (8) to four (4). The average difference in translation/rotation between four markers and eight markers is within 0.2 mm/0.2°.

Table 2 shows the means and standard deviations of differences between the optical tracking system's isocenter displacements and those of CBCT and the second known system in registration tests. The pelvis phantom was initially placed to a treatment position with guidance of the second known system. Detected isocenter displacement was recorded as baseline for each system. The phantom was shifted or rotated with thirteen (13) different combinations within ±20 mm/±5°. Isocenter displacement relative to baseline was recorded for each system. Shown in Table 2 are the mean and one standard deviation of the optical tracking system versus the CBCT and the second (2nd) known system.

lations with the second known system (means<0.22 mm and SDs<0.19 mm) than with CBCT (means<0.44 mm and SDs<0.46 mm) Combined translation deviations in all axes from CBCT and the second known system are 0.74 mm±0.53 mm and 0.42 mm+0.14 mm, respectively. For rotations, the difference in all axes between the optical tracking system and either the CBCT or the second known system were negligible (means<0.2° and SDs<0.1°.

Figure 8:
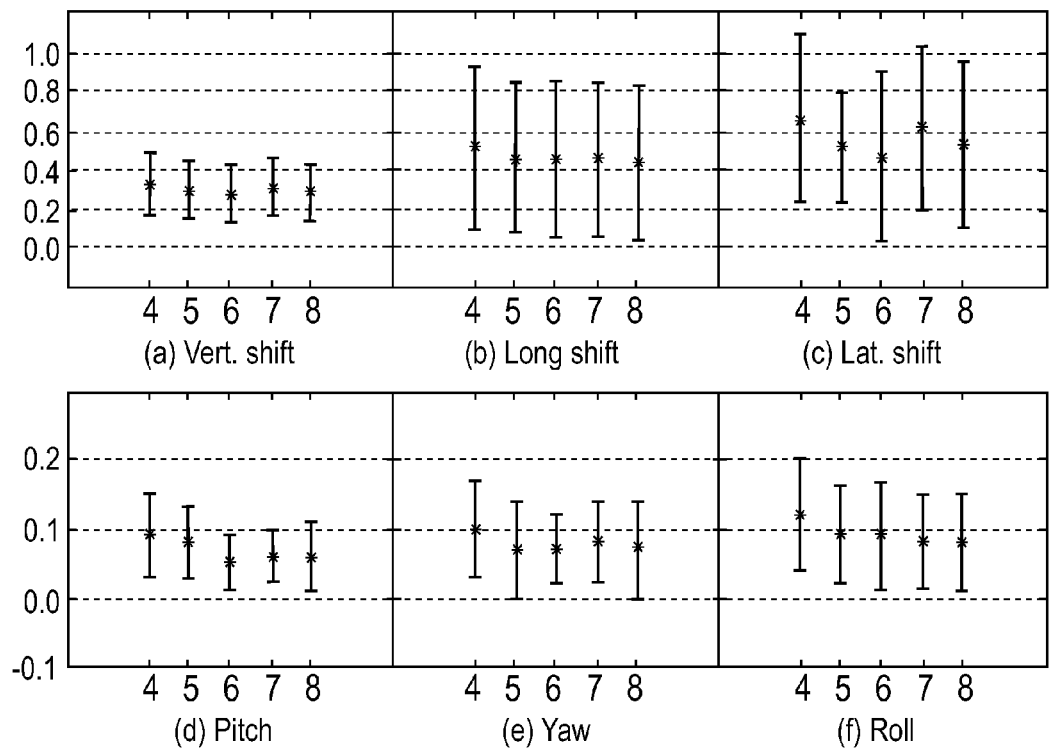
FIG. 8 illustrates an effect of number of markers on registration accuracy of the optical tracking system.

FIG. 8 illustrates an effect of number of markers on registration accuracy of the optical tracking system. Shown are differences of detected isocenter displacement in translation (a-c) and rotation (d-f) of the camera system compared to CBCT. The isocenter displacement is relative to a home position where baseline shift was captured and subtracted. The x-axis represents number of markers range from eight down to four. The y-axis represents difference of shift, in millimeters, in (a-c) and rotation, in degrees, in (d-f). FIG. 8 shows a trend of minor increase in average translation and rotation deviation from CBCT when reducing number of markers from eight (8) to four (4). However, the difference is within 0.2 mm/0.1°.

The performance of automatic ambiguity elimination was assessed with a synthetic marker pattern and a clinical marker pattern.

Figure 9:
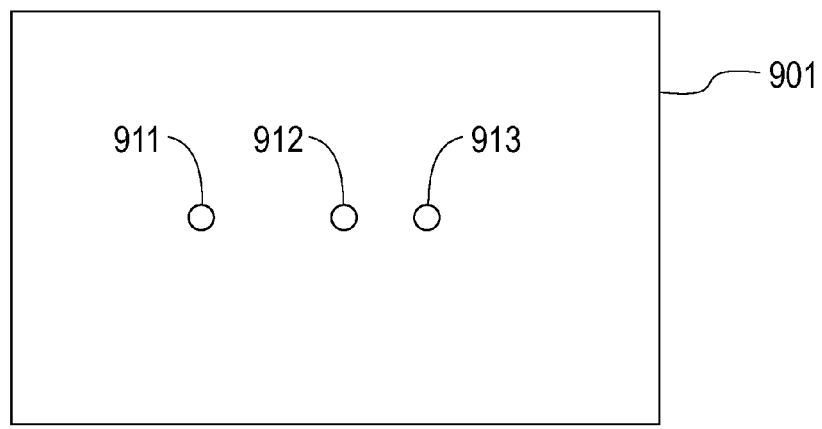
FIGS. 9-12 illustrate an example of ambiguity elimination of a synthetic marker pattern.
Figure 10:
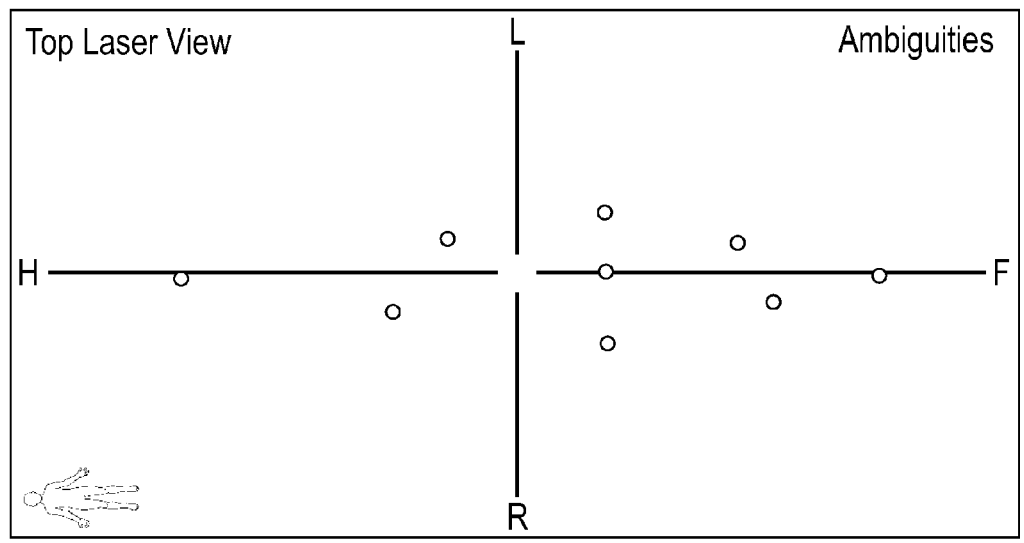
Figure 11:
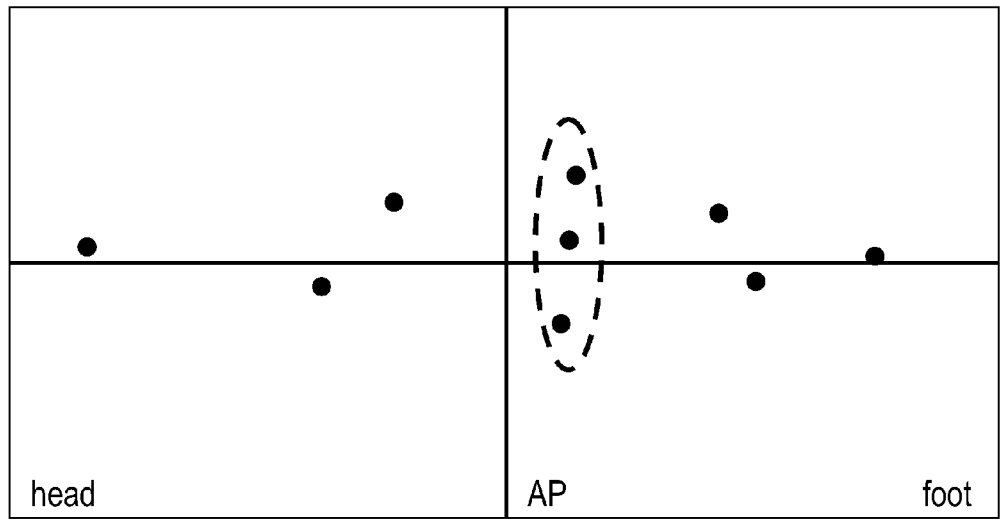
Figure 12:
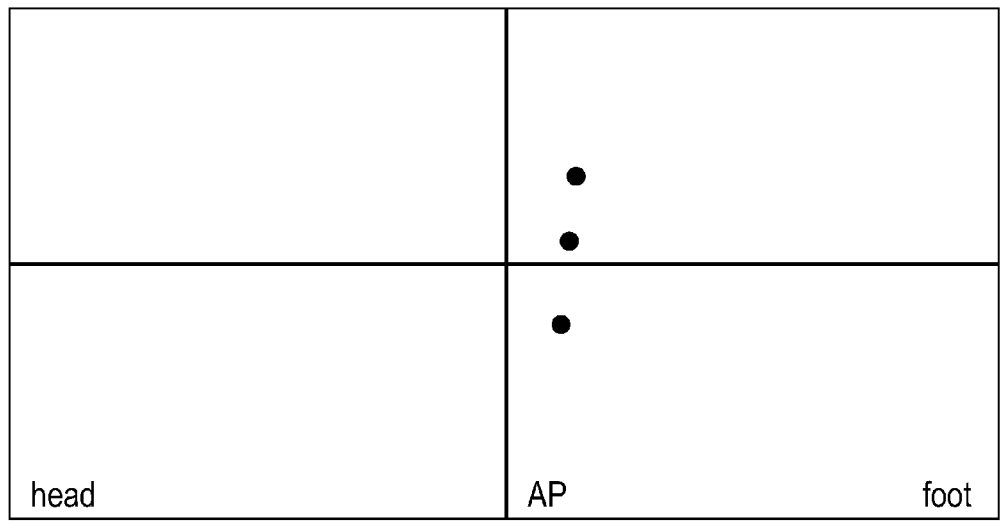

FIGS. 9-12 illustrate an example of ambiguity elimination of a synthetic marker pattern. The synthetic marker pattern is shown in FIG. 9. FIG. 9 shows the three collinear markers 911, 912 and 913 mounted on a plastic board 900 with a smooth surface (with the end of the couch 140 at bottom of the picture). In FIG. 9, an end of the couch 140 is at bottom. Markers observed by the second known system are presented on the display 174, as shown in FIG. 10. Markers observed by the optical tracking system with ambiguity elimination turned off and on are presented on the display 174 as shown in FIGS. 11 and 12, respectively. The three markers circled in FIG. 11 are the true markers. FIGS. 10-12 are AP views with the end of the couch 140 at right of the figures. FIGS. 11 and 12, respectively, show the markers observed by the second known system and the camera system of the optical tracking system in AP view (with the end of the couch 140 at right side of each picture), when the markers were placed parallel to the cameras. Each two of the three true markers created two additional, ambiguous markers as expected, with one closer to the cameras (mounted right above the end of the couch 140) and one farther from the cameras. There were nine (9) total markers in FIGS. 10 and 11, with three (3) true markers vertically located in the middle of the graph (circled on FIG. 11) and three (3) ambiguous markers on either side. FIG. 12 shows the result when the ambiguity elimination algorithm was turned on.

TABLE 2

| N = 13 | Translation (mm) | | | | Rotation (°) | | |
|---|---|---|---|---|---|---|---|
|  | LAT | LONG | VERT | VECT | PITCH | ROLL | YAW |
| vs. CBCT | 0.42 ± 0.46 | 0.44 ± 0.39 | 0.29 ± 0.14 | 0.74 ± 0.53 | 0.06 ± 0.05 | 0.08 ± 0.07 | 0.07 ± 0.07 |
| vs. 2nd | 0.21 ± 0.19 | 0.22 ± 0.15 | 0.20 ± 0.10 | 0.42 ± 0.14 | 0.15 ± 0.10 | 0.08 ± 0.06 | 0.10 ± 0.05 |

The systematic calibration differences between the systems were subtracted from the baseline data. Thirteen combinations of various translations and rotations within the range of ±20 mm and/or ±5° were tested in this study. The optical tracking system showed better agreement in trans- The six (6) ambiguous markers were accurately identified and eliminated which shows the efficacy of ambiguity elimination.

FIGS. 13-16 illustrate an example of ambiguity elimination of a clinic marker pattern of eight (8) markers 1311-

Figure 13:
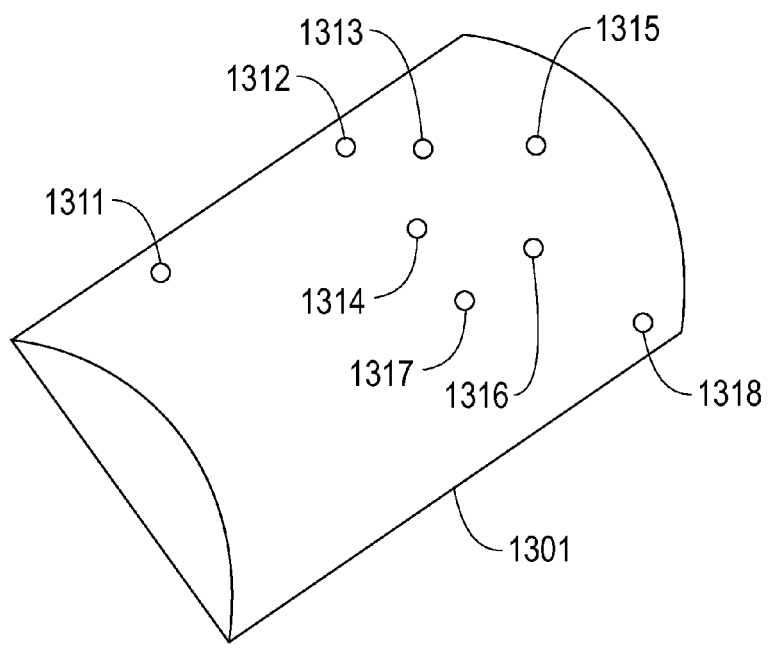
FIGS. 13-16 illustrate an example of ambiguity elimination of a clinic marker pattern.
Figure 14:
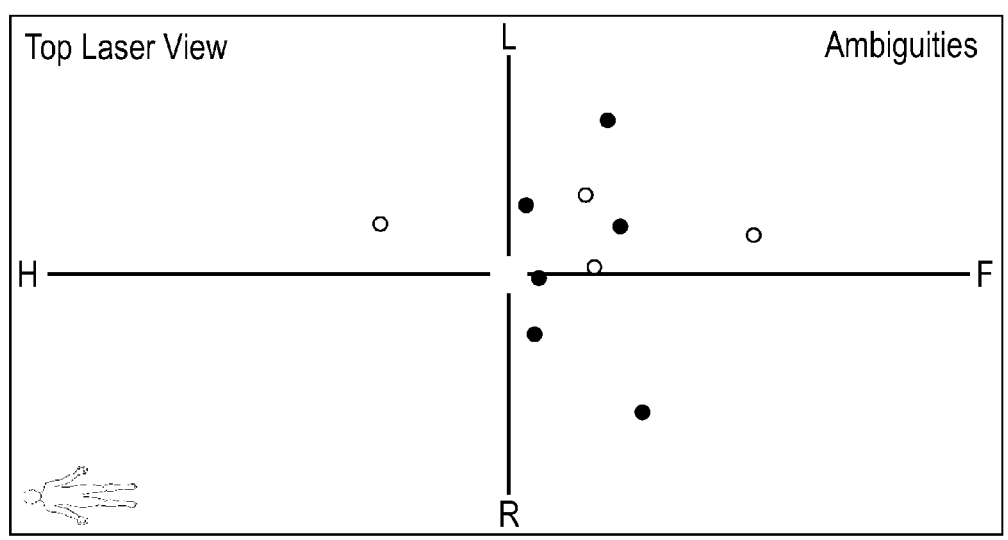
Figure 15:
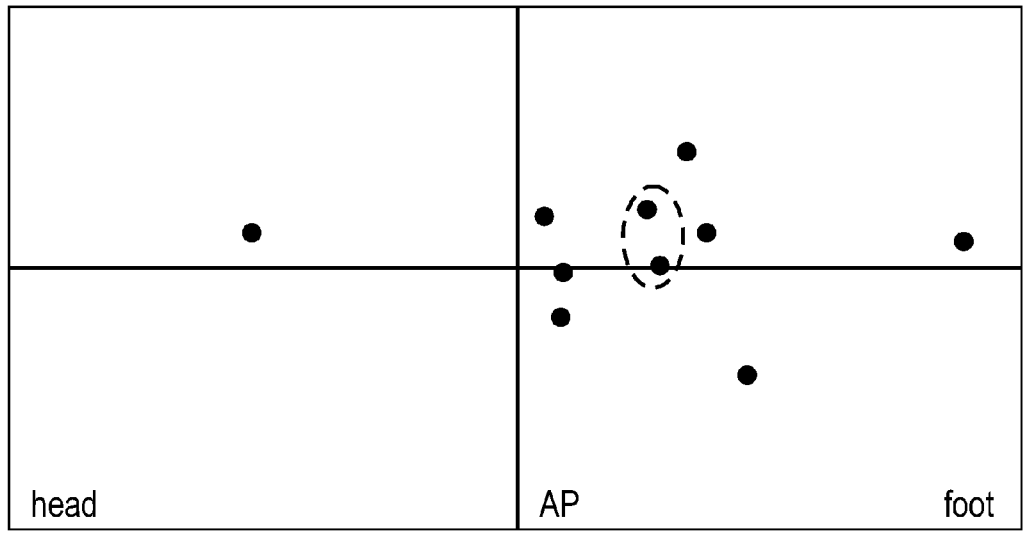
Figure 16:
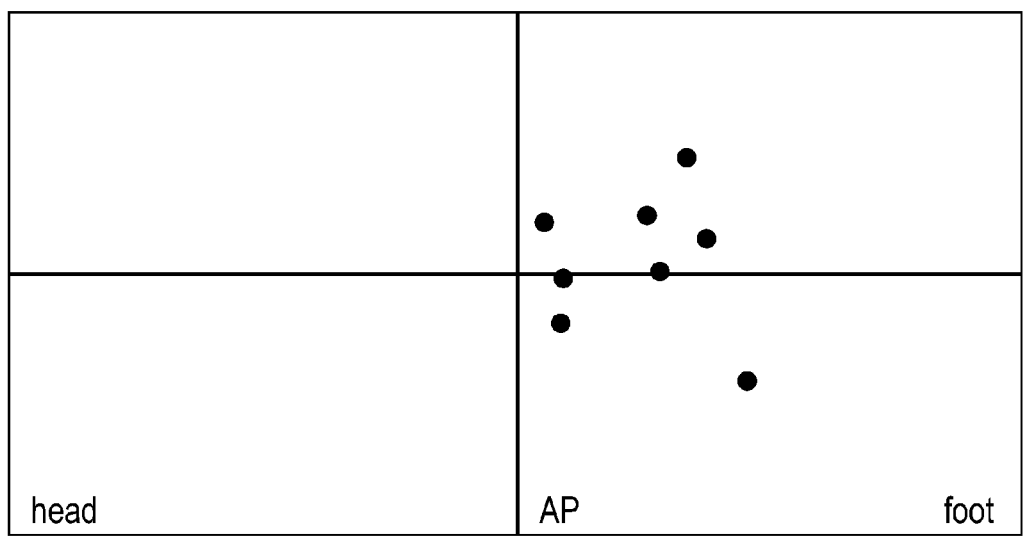

1318 on an anthropomorphic abdomen 1301. In FIG. 13, the end of the couch 140 is at bottom. FIGS. 14-16 are AP views with the end of the couch 140 at right, as presented on the display 174. The two markers causing ambiguities are circled in FIG. 15. Shown in FIG. 14 are the markers observed by the second known system. The results of the optical tracking system with ambiguity elimination turned off and on are shown in FIGS. 15 and 16, respectively. The results on the clinical marker pattern were similar to the results of ambiguity elimination of the synthetic marker pattern. Two ambiguous markers were created, one on the left and one on the far right, as observed by both the second known system and the camera system of the optical tracking system. The two true markers causing the ambiguities were in the middle and circled in FIG. 15. When turning on the automatic ambiguity elimination feature, the optical tracking system accurately removed the ambiguous markers. The resultant pattern shown in FIG. 16 precisely matched the marker pattern placed on the phantom as shown in FIG. 13.

Difference of isocenter displacement between the optical tracking system and the two known systems (CBCT and the second known system) were within 0.5 mm/1° and within 0.5 mm/0.2° in system calibration test and in registration test, respectively. Effect of number of markers in a phantom test that was conducted was negligible with isocenter displacement varying within 0.2 mm/0.2° when reducing number of markers from eight (8) to four (4). The optical tracking system successfully identified and eliminated ambiguous markers in both the synthetic and the clinic marker pattern.

There are several advantages of the optical tracking system over commercially available ones, the most significant being that it is ambiguity free. Extra attention should be paid to placing markers in irregular pattern during CT simulation. Without the optical tracking system, if ambiguous markers show up in the treatment room, one of the two problematic markers is manually blocked to break the condition for ambiguity. This trial-and-error process, typically involving seven (7) to eight (8) markers, is time consuming and leads to significant delay in patient treatment. The optical tracking system can accurately identify and eliminate ambiguous marker which provides considerable flexibility when placing markers. Without the delay caused by the trial-and-error process to manually remove ambiguous markers, the optical tracking system significantly improves workflow in the treatment room.

The ambiguity elimination algorithm starts with determining positions of cameras by creating ambiguous markers with two real markers, based on the principle shown in FIG. 3. Then ambiguous markers are identified based on the factor that they are located at intersections of lines connecting sensors and the source markers; in addition, they are either closer to or farther from cameras than both source markers. The performance of the ambiguity elimination algorithm was demonstrated with a synthetic test case and a clinic case as shown in FIGS. 9-12 and in FIGS. 13-16, respectively. The ambiguity elimination algorithm was found to be robust in realistic situations. Theoretically, the ambiguity elimination algorithm may erroneously remove a true marker if the marker happens to be placed at the position where an ambiguous marker should appear. But the following simple calculation shows that such a theoretical situation will not happen. The two cameras, 50 cm apart, are mounted approximately 200 cm away from machine isocenter and 100 cm vertically above machine gantry rotation axis. The vertical separation of the ambiguous marker position from the source markers increases with the distance between two source markers. For example, a 4 cm separation between two source markers creates approximately 7 cm vertical separation from the ambiguous marker position to the source markers. However, it is not feasible to place a marker 7 cm higher than the other two within 4 cm of the patient's skin.

At least four IR markers are recommended for high precision patient localization and monitoring. A prerequisite to estimate patient orientation and position from multiple marker positions is to establish a one-to-one correspondence between reference markers and optical markers. The backtracking algorithm solves the marker correspondence problem. The backtracking algorithm guarantees to find the optimal solution due to its exhaustive nature. The backtracking algorithm can deal with outlier markers in either set. The backtracking algorithm builds up candidate solutions one marker at a time and validates the newly added marker by checking its distance from other markers. For a newly-added marker to be part of a valid solution, its distances from all previously added markers need to be validated against reference marker set. However, for better efficiency, the distance of a newly-added marker from only two other markers (a first added marker and a marker added immediately prior to the current new-added marker). The majority of the candidate solutions are filtered out by the two-distance check. The error measure of a complete solution, as defined in the marker correspondence section hereinabove, needs to be under the chosen threshold. The optimal solution is a complete solution which wins out by either greater number of matching markers or lower overall error measure. The ability to handle missing markers or misplaced markers by introducing the notion of "null" markers greatly improves the flexibility of the system and the clinic workflow. The system picks up the maximum common subset of markers for patient poise estimation. No last minute adjustment of markers in the treatment room is necessary as long as at least four matching markers can be found.

Experiments have shown that the effect of number of markers on system accuracy is not evident. The difference is within 0.2 mm/0.2° when reducing number of markers from eight (8) to four (4). The results may slightly vary depending on markers pattern and their separations. The test on the motionless phantom does not involve respiratory motion. Individual marker location distortion due to non-uniform motion on the patient's skin may affect the conclusion. Because the overdetermined pose problem is solved with an analytical solution based on least-square estimates, more markers spread out on the patient's skin not only mitigate the effects of measurement noise and distortion, but also better reflect internal motion Improved correlation between internal lung target and external markers has been reported when number of external markers was increased from three (3) to five (5). Further reduction in correlation error is expected when number of markers is increased beyond five (5).

Accuracy of the calibration and registration of optical tracking system is comparable to CBCT as well as the second known system, as validated through tests performed with a pelvis phantom. System calibration is checked by an end-to-end test. Uncertainties due to CT spatial resolution, marker placement reproducibility, camera registration, and CBCT registration are all included in the results. System registration is checked by defining a "home" position and subtracting out the baseline data for each system. For optical cameras, it is achieved by capturing initial marker positions as reference. The aforementioned systematic uncertainties are excluded. A registration test shows better agreement in rotation than calibration test as shown in Table 1 and Table 2. The results on translations are mixed; however, the agreements are all within 0.5 mm in both tests.

The optical tracking system is used for initial patient positioning and real-time monitoring during radiotherapy. The optical tracking system is able to automatically identify and eliminate ambiguous markers, which significantly increases the flexibility to place markers on the patient's skin and improve clinic workflow. The optical tracking system maximizes patient safety by working in synergy with the R&V system to ensure that correct reference data set is loaded. Because it is independent of the couch 140 and gantry, the optical tracking system prevents mistreatment of wrong patient site, especially when treatment target is close to spine or extremities. The optical tracking system has accuracy compared to a commercial optical guidance system and a CBCT system. The optical tracking system plays an important role in patient positioning and motion management.

Figure 17:
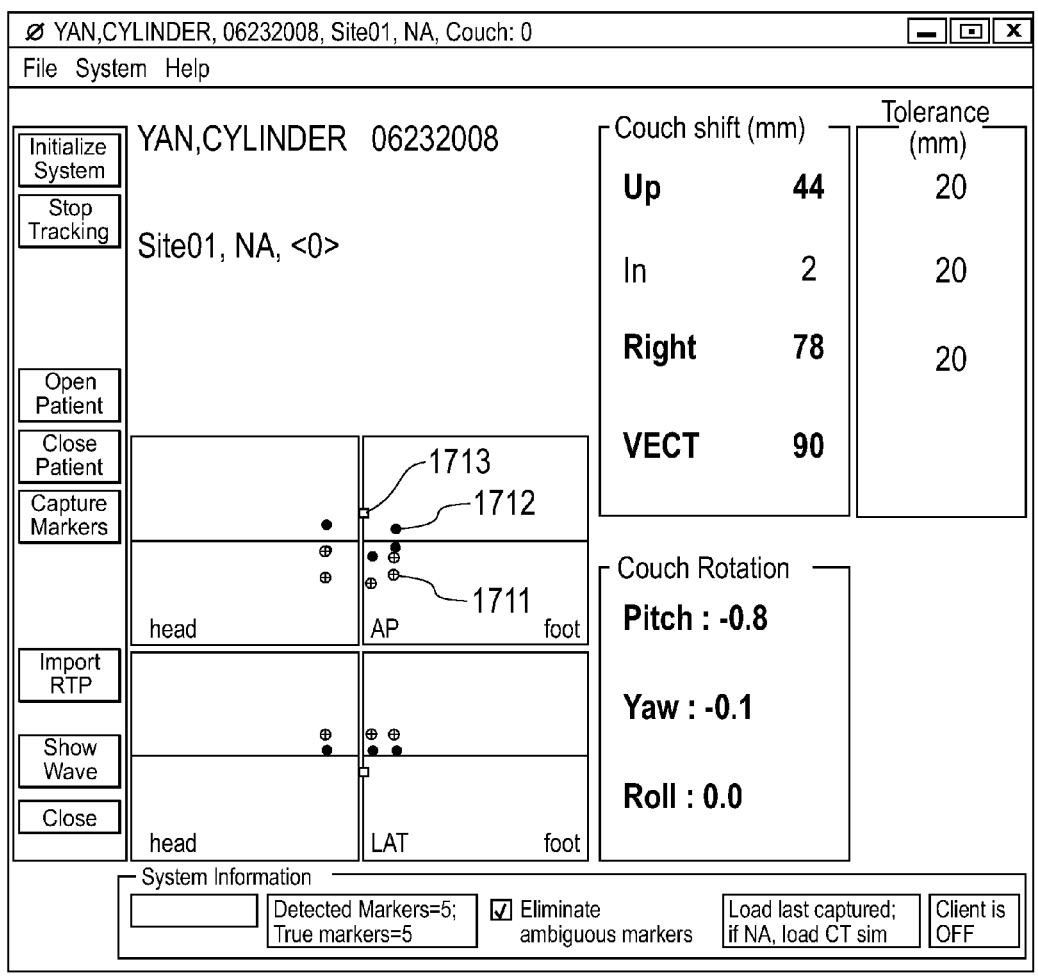
FIG. 17 is an illustration of one embodiment of a graphical user interface of the ambiguity-free optical tracking system, which is presented on the display shown in FIG. 1.

FIG. 17 is an illustration of one embodiment of a graphical user interface (GUI) 1700 of the optical tracking system 101. In one embodiment, the GUI 1700 is presented on the display 174. For the example of FIG. 17, it is assumed that there are five (5) physical markers on the patient 150.

When a treatment beam is loaded in the R&V system, patient's name, field name and reference POIs are retrieved and presented in the GUI 1700. The patient name and field name are shown at a top of the GUI 1700. A difference between predicted marker coordinates and real-time marker coordinates is shown on the top right portion (titled couch shift, measured in millimeter) of the GUI 1700.

An image panel in a lower left portion of the GUI 1700 includes an anteroposterior (AP) view and a lateral (LAT) view. When treating the patient 150, dots appear in the image panel of the GUI 1700 representing predicted marker position and observed real-time marker position. In the image panel, dots of a first type 1711 (in one embodiment, in green color) represent reference markers, and dots of a second type 1712 (in one embodiment, in red color) represent detected markers sensed by the optical tracking system after ambiguous markers have been eliminated.

In an accurate setup (not shown), each detected marker would overlap a corresponding reference marker in the image panel. In such accurate setup, all numbers in the couch shift and rotation would be very small (and within tolerance). On the other hand, in the example of FIG. 17, the test "patient" was intentionally grossly mis-located.

Referring now to the dots of a third type 1713 that are shown in the image panel of the GUI 1700. As is well known, markers are affixed on a patient's skin, but a tumor is typically deeply situated in the patient's body. A goal is to localize the tumor (i.e., a centroid of the tumor) to the isocenter of the treatment room. The dots of the third type 1713 represent the tumor. The two dots of the third type 1713 represent different views, AP and LAT, of the same tumor. The dots of the third type 1713 (tumor) is associated with the dots of the second type 1712 (detected markers). When the patient moves, the dots of the second type 1712 will move within the image panel, and the dots of the third type 1713 will follow the dots of the second type. When all dots of the second type (detected markers) coincide with corresponding dots of the first type (reference markers), the dot of the third type (tumor) will move to origin which indicates the tumor has been perfectly localized to room isocenter (i.e., an accurate setup).

Numbers in the far right of the GUI 1700 are tolerance values (in this example, "20, 20, 20"). When one or more clinic values (in this example, only "in 2") are within corresponding tolerance values, the clinic values are presented in first manner (in one embodiment, in blue color). When one or more clinic values (in this example, "Up 44", "Right 78" and "VECT 90") exceed corresponding tolerance values, the clinic values are presented in a second manner (in one embodiment, in red color) and an alert is issued to indicate errors. The alert may include an audible alert. The system also includes tolerance value for couch rotations, but they are not shown in this example. Numbers in "Couch shift" and "Couch rotation" columns are deviations between a reference marker set and a detected marker set. In this example, the operator needs to move the couch up by 44 mm, in by 2 mm, and right by 78 mm to make the setup accurate. An intentionally wrong setup is shown in this example for pedagogical purposes.

At a bottom of the GUI 1700, there is an area labeled "Detected markers=xx; True markers=xx". An operator (typically, a radiation therapist) usually only cares about couch shift and couch rotation in practice. But, a pattern of true markers are presented in the image panel of the GUI 1700 and are available to the operator if there is a need to investigate. The ambiguity elimination algorithm is completely invisible to the operator. However, the operator can turn on or off the ambiguity elimination feature by entering a checkmark or no checkmark, respectively, in a box at center of the bottom panel of the GUI 1700 labeled "Eliminate ambiguous markers".

The area labeled "Detected markers=xx; True markers=xx" shows how many markers the optical tracking system has seen and how many of them are true markers after ambiguous markers have been identified and eliminated by the ambiguity elimination algorithm. In this example, "Detected markers=5" and "True markers=5"; therefore, no ambiguities are identified.

The optical tracking system 101 has an accuracy that is comparable to CBCT and known commercial optical tracking systems. The optical tracking system 101 significantly enhances the flexibility in marker placement at CT simulation and improves treatment workflow by 1) automatically identifying and eliminating ambiguous markers 2) effectively handling missing, misplaced or occluded markers.

The optical tracking system 101 overcomes shortcomings of the two known commercial systems. The optical tracking system 101 allows a user to affix markers on a patient's skin at any desired positions, which enables its use in stereotactic body radiation therapy treatment for extracranial lesions. Accuracy and consistency of the optical tracking system 101 has been validated against an on-board CBCT system as well as the second known system.

As will be appreciated by one skilled in the art, aspects of the present invention may be embodied as a method, system or computer program product. Accordingly, aspects of the present invention may take the form of an entirely hardware embodiment, an entirely software embodiment (including firmware, resident software, micro-code, etc.) or an embodiment combining software and hardware aspects that may collectively be referred to as a "circuit," "module" or "system". Furthermore, aspects of the present invention may take the form of a computer program product embodied in one or more computer-readable medium(s) having computer-readable program code embodied thereon.

Any combination of one or more computer-readable medium(s) may be utilized. The computer-readable medium may be a computer-readable signal medium or a computer-readable storage medium.

A computer-readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer-readable storage medium would include the following: an electrical connection having one or more wires, a portable computer diskette, a hard disk, a random access memory (RAM), a read-only memory (ROM), an erasable programmable read-only memory (EPROM or flash memory), an optical fiber, a portable compact disc read-only memory (CD-ROM), an optical storage device, a magnetic storage device, or any suitable combination of the foregoing. In the context of this document, a computer-readable storage medium may be any tangible medium that can contain, or store a program for use by or in connection with an instruction execution system, apparatus, or device.

A computer-readable signal medium may include a propagated data signal with computer-readable program code embodied therein, for example, in baseband or as part of a carrier wave. Such a propagated signal may take any of a variety of forms, including, but not limited to, electromagnetic, optical, or any suitable combination thereof. A computer-readable signal medium may be any computer-readable medium that is not a computer-readable storage medium and that can communicate, propagate, or transport a program for use by or in connection with an instruction execution system, apparatus, or device. Computer program code embodied on a computer-readable signal medium may be transmitted using any appropriate medium, including but not limited to wireless, wireline, optical fiber cable, RF, etc., or any suitable combination of the foregoing.

The term "tangible computer-readable storage medium" includes, but is not limited to: solid-state memories such as a memory card or other package that houses one or more read-only (non-volatile) memories, random access memories, or other re-writable (volatile) memories, a magneto-optical or optical medium such as a disk or tape, or other tangible media that can be used to store information. Accordingly, the disclosure is considered to include any one or more of a tangible computer-readable storage medium, as listed herein and including art-recognized equivalents and successor media, in which the software implementations herein are stored.

Computer program code, or computer program instructions, for carrying out operations for aspects of the present invention may be written in any combination of one or more programming languages, including an object oriented programming language such as Java, Smalltalk, C++ or the like, and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The computer program code, or computer program instructions, may also be stored in a computer-readable medium that can direct a computer, other programmable data processing apparatus, or other devices to function in a particular manner, such that the instructions stored in the computer-readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Aspects of the present invention are described above with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. The computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

Dedicated hardware implementations including, but not limited to, application specific integrated circuits, programmable logic arrays and other hardware devices can likewise be constructed to implement the methods described herein. Applications that may include the apparatus and systems of various embodiments broadly include a variety of electronic and computer systems. Some embodiments implement functions in two or more specific interconnected hardware modules or devices with related control and data signals communicated between and through the modules, or as portions of an application-specific integrated circuit. Thus, the example system is applicable to software, firmware, and hardware implementations.

In accordance with various embodiments, the methods described herein are intended for operation as software programs running on a computer processor. Furthermore, software implementations can include, but are not limited to, distributed processing or component/object distributed processing, parallel processing, or virtual machine processing, and can also be constructed to implement the methods described herein.

Although the present specification describes components and functions implemented in the embodiments with reference to particular standards and protocols, the disclosure is not limited to such standards and protocols. Each of the standards for Internet and other packet switched network transmission (e.g., TCP/IP, UDP/IP, HTML, HTTP) represents an example of the state of the art. Such standards are from time-to-time superseded by faster or more efficient equivalents having essentially the same functions. Wireless standards for device detection (e.g., RFID), for short-range communications (e.g., Bluetooth, WiFi, ZigBee), and for long-range communication (e.g., LTE) are contemplated for use by computer 110.

The illustrations of examples described herein are intended to provide a general understanding of the structure of various embodiments, and they are not intended to serve as a complete description of all the elements and features of apparatus and systems that might make use of the structures described herein. Many other embodiments will be apparent to those of skill in the art upon reviewing the above description. Other embodiments may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

Although specific embodiments have been illustrated and described herein, it should be appreciated that any arrangement calculated to achieve the same purpose may be substituted for the specific embodiments shown. The examples herein are intended to cover any and all adaptations or variations of various embodiments. Combinations of the above embodiments, and other embodiments not specifically described herein, are contemplated herein.

The Abstract is provided with the understanding that it is not intended be used to interpret or limit the scope or meaning of the claims. In addition, in the foregoing Detailed Description, various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separately claimed subject matter.

The terminology used herein is for the purpose of describing particular embodiments only and is not intended to be limiting of the invention. As used herein, the singular forms "a", "an" and "the" are intended to include the plural forms as well, unless the context clearly indicates otherwise. It should be understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. The term "another", as used herein, is defined as at least a second or more. The terms "including" and "having," as used herein, are defined as comprising (i.e., open language). The term "coupled," as used herein, is defined as "connected," although not necessarily directly, and not necessarily mechanically. "Communicatively coupled" refers to coupling of components such that these components are able to communicate with one another through, for example, wired, wireless or other communications media. The term "communicatively coupled" or "communicatively coupling" includes, but is not limited to, communicating electronic control signals by which one element may direct or control another. The term "configured to" describes hardware, software or a combination of hardware and software that is adapted to, set up, arranged, built, composed, constructed, designed or that has any combination of these characteristics to carry out a given function. The term "adapted to" describes hardware, software or a combination of hardware and software that is capable of, able to accommodate, to make, or that is suitable to carry out a given function.

The terms "controller", "computer", "processor", "server", "client", "computer system", "computing system", "personal computing system", or "processing system" describe examples of a suitably configured processing system adapted to implement one or more embodiments herein. Any suitably configured processing system is similarly able to be used by embodiments herein, for example and not for limitation, a personal computer, a laptop computer, a tablet computer, a smart phone, a personal digital assistant, a workstation, or the like. A processing system may include one or more processing systems or processors. A processing system can be realized in a centralized fashion in one processing system or in a distributed fashion where different elements are spread across several interconnected processing systems.

The terms "computing system", "computer system", and "personal computing system", describe a processing system that includes a user interface and which is suitably configured and adapted to implement one or more embodiments of the present disclosure. The terms "network", "computer network", "computing network", and "communication network", describe examples of a collection of computers and devices interconnected by communications channels that facilitate communications among users and allows users to share resources. The terms "wireless network", "wireless communication network", and "wireless communication system" describe a network and system that communicatively couples computers and devices primarily or entirely by wireless communication media. The terms "wired network" and "wired communication network" similarly describe a network that communicatively couples computers and devices primarily or entirely by wired communication media.

The corresponding structures, materials, acts, and equivalents of all means or step plus function elements in the claims below are intended to include any structure, material, or act for performing the function in combination with other claimed elements as specifically claimed. The description herein has been given for purposes of illustration and description, but is not intended to be exhaustive or limited to the examples in the form disclosed. Many modifications and variations will be apparent to those of ordinary skill in the art without departing from the scope and spirit of the examples described or claimed. The disclosed embodiments were chosen and described in order to best explain the principles of the embodiments and the practical application, and to enable others of ordinary skill in the art to understand the various embodiments with various modifications as are suited to the particular use contemplated. It is intended that the appended claims below cover any and all such applications, modifications, and variations within the scope of the embodiments.

The terms "a" or "an", as used herein, are defined as one or more than one. The term plurality, as used herein, is defined as two or more than two. The term another, as used herein, is defined as at least a second or more. The terms including and/or having, as used herein, are defined as comprising (i.e., open language). The term coupled, as used herein, is defined as connected, although not necessarily directly, and not necessarily mechanically.

Unless stated otherwise, terms such as "first" and "second" are used to arbitrarily distinguish between the elements such terms describe. Thus, these terms are not necessarily intended to indicate temporal or other prioritization of such elements.

Although specific embodiments of the invention have been disclosed, those having ordinary skill in the art will understand that changes can be made to the specific embodiments without departing from the spirit and scope of the invention. The scope of the invention is not to be restricted, therefore, to the specific embodiments, and it is intended that the appended claims cover any and all such applications, modifications, and embodiments within the scope of the present invention.

What is claimed is:

1. A method of corresponding a set of reference markers $[A_i]$ from a CT scan to a set of optical markers $[B_j]$ detected by cameras in a radiation treatment room, comprising:
   placing retro-reflective markers on a patient;
   performing a CT scan of the patient and the retro-reflective markers;
   assigning x, y, z coordinates to each reference marker of a set of reference markers that appears in the CT scan;
   determining a distance between each reference markers and each of the other reference markers;
   viewing the patient and the retro-reflective markers, with cameras in a radiation treatment room;
   assigning x, y, z coordinates to each optical marker of a set of optical markers created as a result of the viewing;
   determining a distance between each optical marker and each of the other optical markers;
   calculating an error function $E=\Sigma_{i=1}^{N-1} \Sigma_{j=2}^{N} \|d_A(i,j)-d_B(C(i), C(j))\|^2$ in an iterative fashion, where $d_A(i,j)$ denotes distance between two reference markers of the set of reference markers $[A_i]$, $d_B(i,j)$ denotes distance between two optical markers of the set of optical markers $[B_j]$, C is a mapping function that defines an index of an optical marker that corresponds to a reference marker, and N is a number of markers that are mapped; and
   determining a maximum N that minimizes E, subject to:

$E \leq \delta$, and $\|d_A(i,j)-d_B(C(i),C(j))\| \leq \epsilon, \forall i,j \in A,$ where $\delta$ and $\epsilon$ depend on one or more of: CT spatial resolution, CT noise, camera noise, magnitude of motion of the patient near the markers, number of markers, and reproducibility of placement of the markers on the patient.

2. The method of claim 1, including, prior to the step of calculating, adding one or more null reference markers to the set of reference markers when a number of optical markers in the set of optical markers is greater than the number of reference markers in the set of reference markers.

3. The method of claim 1, including, prior to the step of calculating, determining whether one or more optical markers is significantly misplaced, and if so, removing such one or more optical markers from the set of optical markers.

4. A computer program product for corresponding a set of reference markers $[A_i]$ that appears in a CT scan performed on a patient on which were located retro-reflective markers to a set of optical markers $[B_j]$ that were created as a result of the retro-reflective markers being detected by cameras viewing the patient when the CT scan was performed, comprising:
   a non-transitory computer readable medium; and
   computer program instructions for:
   assigning x, y, z coordinates to each reference marker of the set of reference markers,
   determining a distance between each reference markers and each of the other reference markers,
   assigning x, y, z coordinates to each optical marker of a set of optical markers,
   determining a distance between each optical marker and each of the other optical markers,
   calculating an error function $E=\Sigma_{i=1}^{N-1} \Sigma_{j=2}^{N} \|d_A(i,j)-d_B(C(i), C(j))\|^2$ in an iterative fashion, where $d_A(i,j)$ denotes distance between two reference markers of the set of reference markers $[A_i]$, $d_B(i,j)$ denotes distance between two optical markers of the set of optical markers $[B_j]$, C is a mapping function that defines an index of an optical marker that corresponds to a reference marker, and N is a number of markers that are mapped, and
   determining a maximum N that minimizes E, subject to:

$E \leq \delta$, and $\|d_A(i,j)-d_B(C(i),C(j))\| \leq \epsilon, \forall i,j \in A,$ where $\delta$ and $\epsilon$ depend on one or more of: CT spatial resolution, CT noise, camera noise, magnitude of motion of the patient near the markers, number of markers, and reproducibility of placement of the markers on the patient.

5. The computer program product of claim 4, including, prior to the step of calculating, adding one or more null reference markers to the set of reference markers when a number of optical markers in the set of optical markers is greater than the number of reference markers in the set of reference markers.

6. The computer program product of claim 4, including, prior to the step of calculating, determining whether one or more optical markers is significantly misplaced, and if so, removing such one or more optical markers from the set of optical markers.

* * * * *

UNITED STATES PATENT AND TRADEMARK OFFICE
CERTIFICATE OF CORRECTION

PATENT NO. : 9,561,387 B2  
APPLICATION NO. : 14/394353  
DATED : February 7, 2017  
INVENTOR(S) : Guanghua Yan et al.

Page 1 of 1

It is certified that error appears in the above-identified patent and that said Letters Patent is hereby corrected as shown below:

In Item (73) under Assignee, delete "Unitversity" and add --University--

Signed and Sealed this  
Sixth Day of June, 2017

Michelle K. Lee  
*Director of the United States Patent and Trademark Office*